US011787060B2

(12) United States Patent
Wang et al.

(10) Patent No.: US 11,787,060 B2
(45) Date of Patent: Oct. 17, 2023

(54) REMOTE PRESENCE SYSTEM MOUNTED TO OPERATING ROOM HARDWARE

(71) Applicant: TELADOC HEALTH, INC., Purchase, NY (US)

(72) Inventors: Yulun Wang, Goleta, CA (US); Charles S. Jordan, Santa Barbara, CA (US); Marco Pinter, Santa Barbara, CA (US); Daniel Steven Sanchez, Santa Barbara, CA (US); Kevin Hanrahan, Santa Barbara, CA (US)

(73) Assignee: TELADOC HEALTH, INC., Purchase, NY (US)

( * ) Notice: Subject to any disclaimer, the term of this patent is extended or adjusted under 35 U.S.C. 154(b) by 129 days.

(21) Appl. No.: 17/134,751

(22) Filed: Dec. 28, 2020

(65) Prior Publication Data

US 2021/0220998 A1  Jul. 22, 2021

Related U.S. Application Data

(63) Continuation of application No. 12/151,740, filed on May 7, 2008, now Pat. No. 10,875,182.

(Continued)

(51) Int. Cl.
*B25J 9/16* (2006.01)
*B25J 19/02* (2006.01)
(Continued)

(52) U.S. Cl.
CPC ........... *B25J 9/1689* (2013.01); *B25J 19/023* (2013.01); *G16H 20/40* (2018.01); *G16H 40/67* (2018.01); *G16H 80/00* (2018.01)

(58) Field of Classification Search
CPC ....... B25J 9/1689; B25J 19/023; G16H 20/40; G16H 40/67; G16H 80/00; G16H 20/30; G16H 50/20
See application file for complete search history.

(56) References Cited

U.S. PATENT DOCUMENTS 3,821,995 A  7/1974  Aghnides
4,107,689 A  8/1978  Jellinek
(Continued)

FOREIGN PATENT DOCUMENTS

AU  1216200 A  5/2000
CA  2289697 A1  11/1998
(Continued)

OTHER PUBLICATIONS

Screenshot Showing Google Date for Lemaire Telehealth Manual, screenshot retrieved on Dec. 18, 2014, 1 page.
(Continued)

*Primary Examiner* — Bhavesh V Amin

(57) ABSTRACT

A robot system that includes a remote station and a robot face. The robot face includes a camera that is coupled to a monitor of the remote station and a monitor that is coupled to a camera of the remote station. The robot face and remote station also have speakers and microphones that are coupled together. The robot face may be coupled to a boom. The boom can extend from the ceiling of a medical facility. Alternatively, the robot face may be attached to a medical table with an attachment mechanism. The robot face and remote station allows medical personnel to provide medical consultation through the system.

20 Claims, 6 Drawing Sheets

Related U.S. Application Data

(60) Provisional application No. 61/070,348, filed on Mar. 20, 2008.

(51) Int. Cl.
  *G16H 80/00* (2018.01)
  *G16H 20/40* (2018.01)
  *G16H 40/67* (2018.01)

(56) References Cited

U.S. PATENT DOCUMENTS

| | | |
|---|---|---|
| 4,213,182 A | 7/1980 | Eichelberger et al. |
| 4,413,693 A | 11/1983 | Derby |
| 4,471,354 A | 9/1984 | Smith |
| 4,519,466 A | 5/1985 | Shiraishi |
| 4,553,309 A | 11/1985 | Hess et al. |
| 4,572,594 A | 2/1986 | Schwartz |
| 4,625,274 A | 11/1986 | Schroeder |
| 4,638,445 A | 1/1987 | Mattaboni |
| 4,652,204 A | 3/1987 | Arnett |
| 4,669,168 A | 6/1987 | Tamura et al. |
| 4,679,152 A | 7/1987 | Perdue |
| 4,697,278 A | 9/1987 | Fleischer |
| 4,697,472 A | 10/1987 | Hiyane |
| 4,709,265 A | 11/1987 | Silverman et al. |
| 4,733,737 A | 3/1988 | Falamak |
| 4,751,658 A | 6/1988 | Kadonoff et al. |
| 4,766,581 A | 8/1988 | Korn et al. |
| 4,777,416 A | 10/1988 | Georg et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,878,501 A | 11/1989 | Shue |
| 4,942,512 A | 7/1990 | Kohno |
| 4,942,538 A | 7/1990 | Yuan et al. |
| 4,953,159 A | 8/1990 | Hayden et al. |
| 4,974,607 A | 12/1990 | Miwa |
| 4,977,971 A | 12/1990 | Cran et al. |
| 5,006,988 A | 4/1991 | Borenstein et al. |
| 5,040,116 A | 8/1991 | Evans, Jr. et al. |
| 5,051,906 A | 9/1991 | Evans, Jr. et al. |
| 5,073,749 A | 12/1991 | Kanayama |
| 5,084,828 A | 1/1992 | Kaufman et al. |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,182,641 A | 1/1993 | Diner et al. |
| 5,186,270 A | 2/1993 | West |
| 5,193,143 A | 3/1993 | Kaemmerer et al. |
| 5,217,453 A | 6/1993 | Wilk |
| 5,220,263 A | 6/1993 | Onishi et al. |
| 5,224,157 A | 6/1993 | Yamada et al. |
| 5,230,023 A | 7/1993 | Nakano |
| 5,231,693 A | 7/1993 | Backes et al. |
| 5,236,432 A | 8/1993 | Matse et al. |
| 5,262,944 A | 11/1993 | Weisner et al. |
| 5,305,427 A | 4/1994 | Nagata |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,341,854 A | 8/1994 | Zezulka et al. |
| 5,347,306 A | 9/1994 | Nitta |
| 5,347,457 A | 9/1994 | Tanaka et al. |
| 5,350,033 A | 9/1994 | Kraft |
| 5,366,896 A | 11/1994 | Margrey et al. |
| 5,374,879 A | 12/1994 | Pin et al. |
| 5,375,195 A | 12/1994 | Johnston |
| 5,400,068 A | 3/1995 | Ishida et al. |
| 5,413,693 A | 5/1995 | Redepenning |
| 5,417,210 A | 5/1995 | Funda et al. |
| 5,419,008 A | 5/1995 | West |
| 5,436,542 A | 7/1995 | Petelin et al. |
| 5,441,042 A | 8/1995 | Putman |
| 5,441,047 A | 8/1995 | David et al. |
| 5,442,728 A | 8/1995 | Kaufman et al. |
| 5,462,051 A | 10/1995 | Oka et al. |
| 5,486,853 A | 1/1996 | Baxter et al. |
| 5,510,832 A | 4/1996 | Garcia |
| 5,511,147 A | 4/1996 | Abdel-Malek |
| 5,525,905 A | 6/1996 | Mohapatra et al. |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,563,998 A | 10/1996 | Yaksich et al. |
| 5,572,229 A | 11/1996 | Fisher |
| 5,572,999 A | 11/1996 | Funda et al. |
| 5,594,859 A | 1/1997 | Palmer et al. |
| 5,600,573 A | 2/1997 | Hendricks et al. |
| 5,603,328 A | 2/1997 | Zucker et al. |
| 5,617,539 A | 4/1997 | Ludwig et al. |
| 5,619,341 A | 4/1997 | Auyeung et al. |
| 5,623,679 A | 4/1997 | Rivette et al. |
| 5,630,566 A | 5/1997 | Case |
| 5,636,218 A | 6/1997 | Ishikawa et al. |
| 5,652,849 A | 7/1997 | Conway et al. |
| 5,657,246 A | 8/1997 | Hogan et al. |
| 5,659,779 A | 8/1997 | Laird et al. |
| 5,673,082 A | 9/1997 | Wells et al. |
| 5,675,229 A | 10/1997 | Thorne |
| 5,682,199 A | 10/1997 | Lankford |
| 5,684,531 A | 11/1997 | Li et al. |
| 5,684,695 A | 11/1997 | Bauer |
| 5,701,904 A | 12/1997 | Simmons et al. |
| 5,715,548 A | 2/1998 | Weismiller et al. |
| 5,734,805 A | 3/1998 | Isensee et al. |
| 5,739,657 A | 4/1998 | Takayama et al. |
| 5,748,629 A | 5/1998 | Caldara et al. |
| 5,749,058 A | 5/1998 | Hashimoto |
| 5,749,362 A | 5/1998 | Funda et al. |
| 5,754,631 A | 5/1998 | Cave |
| 5,758,079 A | 5/1998 | Ludwig et al. |
| 5,762,458 A | 6/1998 | Wang et al. |
| 5,764,731 A | 6/1998 | Yablon |
| 5,767,897 A | 6/1998 | Howell |
| 5,786,846 A | 7/1998 | Hiroaki |
| 5,787,545 A | 8/1998 | Colens |
| 5,793,365 A | 8/1998 | Tang et al. |
| 5,799,055 A | 8/1998 | Peshkin et al. |
| 5,801,755 A | 9/1998 | Echerer |
| 5,802,494 A | 9/1998 | Kuno |
| 5,836,872 A | 11/1998 | Kenet et al. |
| 5,838,575 A | 11/1998 | Lion |
| 5,844,599 A | 12/1998 | Hildin |
| 5,857,534 A | 1/1999 | DeVault et al. |
| 5,867,494 A | 2/1999 | Krishnaswamy et al. |
| 5,867,653 A | 2/1999 | Aras et al. |
| 5,871,451 A | 2/1999 | Unger et al. |
| 5,872,922 A | 2/1999 | Hogan et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober |
| 5,954,692 A | 9/1999 | Smith et al. |
| 5,959,423 A | 9/1999 | Nakanishi et al. |
| 5,961,446 A | 10/1999 | Beller et al. |
| 5,966,130 A | 10/1999 | Benman, Jr. |
| 5,973,724 A | 10/1999 | Riddle |
| 5,974,446 A | 10/1999 | Sonnenreich et al. |
| 5,983,263 A | 11/1999 | Rothrock et al. |
| 5,995,119 A | 11/1999 | Cosatto et al. |
| 5,995,884 A | 11/1999 | Allen et al. |
| 5,999,977 A | 12/1999 | Riddle |
| 6,006,946 A | 12/1999 | Williams et al. |
| 6,031,845 A | 2/2000 | Walding |
| 6,036,812 A | 3/2000 | Williams et al. |
| 6,047,259 A | 4/2000 | Campbell et al. |
| 6,091,219 A | 7/2000 | Maruo et al. |

(56) References Cited

U.S. PATENT DOCUMENTS

| | | |
|---|---|---|
| 6,113,343 A | 9/2000 | Goldenberg et al. |
| 6,133,944 A | 10/2000 | Braun et al. |
| 6,135,228 A | 10/2000 | Asada et al. |
| 6,148,100 A | 11/2000 | Anderson et al. |
| 6,160,582 A | 12/2000 | Hill |
| 6,170,929 B1 | 1/2001 | Wilson et al. |
| 6,175,779 B1 | 1/2001 | Barrett |
| 6,189,034 B1 | 2/2001 | Riddle |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba et al. |
| 6,233,504 B1 | 5/2001 | Das et al. |
| 6,233,735 B1 | 5/2001 | Ebihara |
| 6,250,928 B1 | 6/2001 | Poggio et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,292,714 B1 | 9/2001 | Okabayashi |
| 6,304,050 B1 | 10/2001 | Skaar et al. |
| 6,313,853 B1 | 11/2001 | Lamontagne et al. |
| 6,314,631 B1 | 11/2001 | Pryor |
| 6,317,652 B1 | 11/2001 | Osada |
| 6,317,953 B1 | 11/2001 | Pryor |
| 6,321,137 B1 | 11/2001 | De Smet |
| 6,324,184 B1 | 11/2001 | Hou et al. |
| 6,324,443 B1 | 11/2001 | Kurakake et al. |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,331,181 B1 | 12/2001 | Tierney et al. |
| 6,346,950 B1 | 2/2002 | Jouppi |
| 6,346,962 B1 | 2/2002 | Goodridge |
| 6,369,847 B1 | 4/2002 | James et al. |
| 6,373,855 B1 | 4/2002 | Downing et al. |
| 6,381,515 B1 | 4/2002 | Inoue et al. |
| 6,389,329 B1 | 5/2002 | Colens |
| 6,400,378 B1 | 6/2002 | Snook |
| 6,408,230 B2 | 6/2002 | Wada |
| 6,411,055 B1 | 6/2002 | Fujita et al. |
| 6,430,471 B1 | 8/2002 | Kintou et al. |
| 6,430,475 B2 | 8/2002 | Okamoto et al. |
| 6,438,457 B1 | 8/2002 | Yokoo et al. |
| 6,445,964 B1 | 9/2002 | White et al. |
| 6,449,762 B1 | 9/2002 | McElvain |
| 6,452,915 B1 | 9/2002 | Jorgensen |
| 6,457,043 B1 | 9/2002 | Kwak et al. |
| 6,459,955 B1 | 10/2002 | Bartsch et al. |
| 6,463,352 B1 | 10/2002 | Tadokoro et al. |
| 6,463,361 B1 | 10/2002 | Wang et al. |
| 6,466,844 B1 | 10/2002 | Ikeda et al. |
| 6,468,265 B1 | 10/2002 | Evans et al. |
| 6,470,235 B2 | 10/2002 | Kasuga et al. |
| 6,474,434 B1 | 11/2002 | Bech |
| 6,480,762 B1 | 11/2002 | Uchikubo et al. |
| 6,491,701 B2 | 12/2002 | Tierney et al. |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury, Jr. et al. |
| 6,523,629 B1 | 2/2003 | Buttz et al. |
| 6,526,332 B2 | 2/2003 | Sakamoto et al. |
| 6,529,620 B2 | 3/2003 | Thompson |
| 6,529,765 B1 | 3/2003 | Franck et al. |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu et al. |
| 6,543,899 B2 | 4/2003 | Covannon et al. |
| 6,549,215 B2 | 4/2003 | Jouppi |
| 6,563,533 B1 | 5/2003 | Colby |
| 6,567,038 B1 | 5/2003 | Granot et al. |
| 6,580,246 B2 | 6/2003 | Jacobs |
| 6,581,798 B2 | 6/2003 | Liff et al. |
| 6,584,376 B1 | 6/2003 | Van Kommer |
| 6,587,750 B2 | 7/2003 | Gerbi et al. |
| 6,590,604 B1 | 7/2003 | Tucker et al. |
| 6,594,269 B1 | 7/2003 | Polcyn |
| 6,594,552 B1 | 7/2003 | Nowlin et al. |
| 6,597,392 B1 | 7/2003 | Jenkins et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,611,120 B2 | 8/2003 | Song et al. |
| 6,643,496 B1 | 11/2003 | Shimoyama et al. |
| 6,646,677 B2 | 11/2003 | Noro et al. |
| 6,650,748 B1 | 11/2003 | Edwards et al. |
| 6,666,374 B1 | 12/2003 | Green et al. |
| 6,667,592 B2 | 12/2003 | Jacobs et al. |
| 6,674,259 B1 | 1/2004 | Norman et al. |
| 6,684,129 B2 | 1/2004 | Salisbury, Jr. et al. |
| 6,691,000 B2 | 2/2004 | Nagai et al. |
| 6,693,585 B1 | 2/2004 | MacLeod |
| 6,710,797 B1 | 3/2004 | McNelley et al. |
| 6,724,823 B2 | 4/2004 | Rovati et al. |
| 6,728,599 B2 | 4/2004 | Wang et al. |
| 6,763,282 B2 | 7/2004 | Glenn et al. |
| 6,763,284 B2 | 7/2004 | Watanabe et al. |
| 6,764,373 B1 | 7/2004 | Osawa et al. |
| 6,769,771 B2 | 8/2004 | Trumbull |
| 6,781,606 B2 | 8/2004 | Jouppi |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,816,192 B1 | 11/2004 | Nishikawa |
| 6,816,754 B2 | 11/2004 | Mukai et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,893,267 B1 | 5/2005 | Yueh |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe et al. |
| 6,957,712 B2 | 10/2005 | Song et al. |
| 6,958,706 B2 | 10/2005 | Chaco et al. |
| 6,965,394 B2 | 11/2005 | Gutta et al. |
| 6,990,112 B1 | 1/2006 | Brent et al. |
| 6,995,664 B1 | 2/2006 | Darling |
| 7,007,235 B1 | 2/2006 | Hussein et al. |
| 7,011,538 B2 | 3/2006 | Chang |
| 7,015,934 B2 | 3/2006 | Toyama et al. |
| RE39,080 E | 4/2006 | Johnston |
| 7,030,757 B2 | 4/2006 | Matsuhira et al. |
| 7,053,578 B2 | 5/2006 | Diehl et al. |
| 7,055,210 B2 | 6/2006 | Keppler et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | McLurkin et al. |

(56) References Cited

U.S. PATENT DOCUMENTS

| | | |
|---|---|---|
| 7,123,285 B2 | 10/2006 | Smith et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Liff et al. |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 | 1/2007 | Wang et al. |
| 7,158,861 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,164,970 B2 * | 1/2007 | Wang .................. B25J 19/022 600/595 |
| 7,167,448 B2 | 1/2007 | Wookey et al. |
| 7,171,286 B2 | 1/2007 | Wang et al. |
| 7,174,238 B1 | 2/2007 | Zweig |
| 7,181,455 B2 | 2/2007 | Wookey et al. |
| 7,184,559 B2 | 2/2007 | Jouppi |
| 7,188,000 B2 | 3/2007 | Chiappetta et al. |
| 7,199,790 B2 | 4/2007 | Rosenberg et al. |
| 7,202,851 B2 | 4/2007 | Cunningham et al. |
| 7,206,627 B2 | 4/2007 | Abovitz et al. |
| 7,215,786 B2 | 5/2007 | Nakadai et al. |
| 7,219,364 B2 | 5/2007 | Bolle et al. |
| 7,222,000 B2 * | 5/2007 | Wang .................. B25J 9/1689 600/595 |
| 7,227,334 B2 | 6/2007 | Yang et al. |
| 7,256,708 B2 | 8/2007 | Rosenfeld et al. |
| 7,262,573 B2 | 8/2007 | Wang et al. |
| 7,283,153 B2 | 10/2007 | Provost et al. |
| 7,289,883 B2 | 10/2007 | Wang et al. |
| 7,292,257 B2 | 11/2007 | Kang et al. |
| 7,292,912 B2 | 11/2007 | Wang et al. |
| 7,305,114 B2 | 12/2007 | Wolff et al. |
| 7,317,685 B1 | 1/2008 | Flott et al. |
| 7,321,807 B2 | 1/2008 | Laski |
| 7,332,890 B2 | 2/2008 | Cohen et al. |
| 7,333,642 B2 | 2/2008 | Green |
| 7,346,429 B2 | 3/2008 | Goldenberg et al. |
| 7,352,153 B2 | 4/2008 | Yan |
| 7,363,121 B1 | 4/2008 | Chen et al. |
| 7,382,399 B1 | 6/2008 | McCall et al. |
| 7,386,730 B2 | 6/2008 | Uchikubo |
| 7,391,432 B2 | 6/2008 | Terada |
| 7,400,578 B2 | 7/2008 | Guthrie et al. |
| 7,404,140 B2 | 7/2008 | O'Rourke |
| 7,421,470 B2 | 9/2008 | Ludwig et al. |
| 7,430,209 B2 | 9/2008 | Porter |
| 7,432,949 B2 | 10/2008 | Remy et al. |
| 7,433,921 B2 | 10/2008 | Ludwig et al. |
| 7,441,953 B2 | 10/2008 | Banks |
| 7,467,211 B1 | 12/2008 | Herman et al. |
| 7,483,867 B2 | 1/2009 | Ansari et al. |
| 7,492,731 B2 | 2/2009 | Hagendorf |
| 7,510,428 B2 | 3/2009 | Obata et al. |
| 7,523,069 B1 | 4/2009 | Friedl et al. |
| 7,525,281 B2 | 4/2009 | Koyanagi et al. |
| 7,535,486 B2 | 5/2009 | Motomura et al. |
| 7,557,758 B2 | 7/2009 | Rofougaran |
| 7,587,260 B2 | 9/2009 | Bruemmer et al. |
| 7,587,512 B2 | 9/2009 | Ta et al. |
| 7,590,060 B2 | 9/2009 | Miceli |
| 7,593,030 B2 | 9/2009 | Wang et al. |
| 7,599,290 B2 | 10/2009 | Dos Remedios et al. |
| 7,624,166 B2 | 11/2009 | Foote et al. |
| 7,626,569 B2 * | 12/2009 | Lanier .................. G06F 3/012 348/42 |
| 7,630,314 B2 | 12/2009 | Dos Remedios et al. |
| 7,631,833 B1 | 12/2009 | Ghaleb et al. |
| 7,643,051 B2 | 1/2010 | Sandberg et al. |
| 7,647,320 B2 | 1/2010 | Mok et al. |
| 7,657,560 B1 | 2/2010 | DiRienzo |
| 7,680,038 B1 | 3/2010 | Gourlay |
| 7,693,757 B2 | 4/2010 | Zimmerman |
| 7,698,432 B2 | 4/2010 | Short et al. |
| 7,703,113 B2 | 4/2010 | Dawson |
| 7,719,229 B2 | 5/2010 | Kaneko et al. |
| 7,720,572 B2 | 5/2010 | Ziegler et al. |
| 7,737,993 B2 | 6/2010 | Kaasila et al. |
| 7,739,383 B1 | 6/2010 | Short et al. |
| 7,756,614 B2 | 7/2010 | Jouppi |
| 7,761,185 B2 * | 7/2010 | Wang .................. A61B 34/35 700/259 |
| 7,769,492 B2 * | 8/2010 | Wang .................. G16H 80/00 700/257 |
| 7,769,705 B1 | 8/2010 | Luechtefeld |
| 7,774,158 B2 | 8/2010 | Domingues Goncalves et al. |
| 7,797,168 B2 | 9/2010 | Kusumoto et al. |
| 7,813,836 B2 | 10/2010 | Wang et al. |
| 7,831,575 B2 | 11/2010 | Trossell et al. |
| 7,835,775 B2 | 11/2010 | Sawayama et al. |
| 7,860,680 B2 | 12/2010 | Arms et al. |
| 7,861,366 B2 | 1/2011 | Hahm et al. |
| 7,885,822 B2 | 2/2011 | Akers et al. |
| 7,890,382 B2 | 2/2011 | Robb et al. |
| 7,912,583 B2 | 3/2011 | Gutmann et al. |
| RE42,288 E | 4/2011 | Degioanni |
| 7,924,323 B2 | 4/2011 | Walker et al. |
| 7,949,616 B2 | 5/2011 | Levy et al. |
| 7,956,894 B2 | 6/2011 | Akers et al. |
| 7,957,837 B2 | 6/2011 | Ziegler et al. |
| 7,982,763 B2 * | 7/2011 | King .................. A61B 90/361 348/14.02 |
| 7,982,769 B2 | 7/2011 | Jenkins et al. |
| 7,987,069 B2 | 7/2011 | Rodgers et al. |
| 7,995,652 B2 | 8/2011 | Washington |
| 7,996,264 B2 | 8/2011 | Kusumoto et al. |
| 8,049,678 B2 | 11/2011 | Lee et al. |
| 8,072,481 B1 | 12/2011 | McNelley et al. |
| 8,077,963 B2 | 12/2011 | Wang et al. |
| 8,116,910 B2 | 2/2012 | Walters et al. |
| 8,126,960 B2 | 2/2012 | Obradovich et al. |
| 8,160,745 B2 * | 4/2012 | Sugiura .................. B25J 9/1666 901/1 |
| 8,170,241 B2 | 5/2012 | Roe et al. |
| 8,179,418 B2 | 5/2012 | Wright et al. |
| 8,180,486 B2 | 5/2012 | Saito et al. |
| 8,209,051 B2 | 6/2012 | Wang et al. |
| 8,212,533 B2 | 7/2012 | Ota |
| 8,265,793 B2 | 9/2012 | Cross et al. |
| 8,287,522 B2 | 10/2012 | Moses et al. |
| 8,292,807 B2 | 10/2012 | Perkins et al. |
| 8,320,534 B2 | 11/2012 | Kim et al. |
| 8,340,654 B2 | 12/2012 | Bratton et al. |
| 8,340,819 B2 | 12/2012 | Mangaser et al. |
| 8,348,675 B2 | 1/2013 | Dohrmann |
| 8,374,171 B2 | 2/2013 | Cho et al. |
| 8,384,755 B2 * | 2/2013 | Wang .................. H04N 7/147 348/14.05 |
| 8,400,491 B1 | 3/2013 | Panpaliya et al. |
| 8,401,275 B2 | 3/2013 | Wang et al. |
| 8,423,284 B2 | 4/2013 | O'Shea |
| 8,451,731 B1 | 5/2013 | Lee et al. |
| 8,463,435 B2 | 6/2013 | Herzog et al. |
| 8,489,641 B1 | 7/2013 | Seefeld et al. |
| 8,503,340 B1 | 8/2013 | Xu |
| 8,515,577 B2 | 8/2013 | Wang et al. |
| 8,527,094 B2 | 9/2013 | Kumar et al. |
| 8,531,502 B2 | 9/2013 | Cheng et al. |
| 8,532,860 B2 | 9/2013 | Daly |
| 8,588,976 B2 | 11/2013 | Mangaser et al. |
| 8,610,786 B2 | 12/2013 | Ortiz |
| 8,612,051 B2 | 12/2013 | Norman et al. |
| 8,639,797 B1 | 1/2014 | Pan et al. |
| 8,670,017 B2 | 3/2014 | Stuart et al. |
| 8,726,454 B2 | 5/2014 | Gilbert, Jr. et al. |
| 8,750,906 B2 | 6/2014 | Winkler et al. |

(56) References Cited

U.S. PATENT DOCUMENTS

| | | | |
|---|---|---|---|
| 8,754,925 B2 * | 6/2014 | Ng | H04N 7/142 |
| | | | 348/14.05 |
| 8,776,043 B1 | 7/2014 | Thimsen et al. | |
| 8,780,165 B2 * | 7/2014 | Wang | G16H 40/67 |
| | | | 348/14.05 |
| 8,836,751 B2 | 9/2014 | Ballantyne et al. | |
| 8,849,679 B2 | 9/2014 | Wang et al. | |
| 8,849,680 B2 | 9/2014 | Wright et al. | |
| 8,861,750 B2 | 10/2014 | Roe et al. | |
| 8,897,920 B2 | 11/2014 | Wang et al. | |
| 8,902,278 B2 | 12/2014 | Pinter et al. | |
| 8,983,174 B2 | 3/2015 | Wang et al. | |
| 8,994,776 B2 | 3/2015 | Sutherland et al. | |
| 8,996,165 B2 * | 3/2015 | Wang | A61B 5/7465 |
| | | | 348/14.02 |
| 9,014,848 B2 | 4/2015 | Farlow et al. | |
| 9,089,972 B2 | 7/2015 | Stuart et al. | |
| 9,098,611 B2 | 8/2015 | Pinter et al. | |
| 9,147,284 B2 | 9/2015 | Keene et al. | |
| 9,440,356 B2 | 9/2016 | Sutherland et al. | |
| 9,715,337 B2 | 7/2017 | Ballantyne et al. | |
| 2001/0002448 A1 | 5/2001 | Wilson et al. | |
| 2001/0010053 A1 | 7/2001 | Ben-Shachar et al. | |
| 2001/0010541 A1 | 8/2001 | Fernandez et al. | |
| 2001/0020200 A1 | 9/2001 | Das et al. | |
| 2001/0034475 A1 | 10/2001 | Flach et al. | |
| 2001/0034544 A1 | 10/2001 | Mo | |
| 2001/0037163 A1 | 11/2001 | Allard | |
| 2001/0048464 A1 | 12/2001 | Barnett | |
| 2001/0051881 A1 | 12/2001 | Filler | |
| 2001/0054071 A1 | 12/2001 | Loeb | |
| 2001/0055373 A1 | 12/2001 | Yamashita | |
| 2002/0010596 A1 | 1/2002 | Matory | |
| 2002/0015296 A1 | 2/2002 | Howell et al. | |
| 2002/0027597 A1 | 3/2002 | Sachau | |
| 2002/0027652 A1 | 3/2002 | Paromtchik et al. | |
| 2002/0033880 A1 | 3/2002 | Sul et al. | |
| 2002/0038168 A1 | 3/2002 | Kasuga et al. | |
| 2002/0044201 A1 | 4/2002 | Alexander et al. | |
| 2002/0049517 A1 | 4/2002 | Ruffner | |
| 2002/0055917 A1 | 5/2002 | Muraca | |
| 2002/0057279 A1 | 5/2002 | Jouppi | |
| 2002/0058929 A1 | 5/2002 | Green | |
| 2002/0059587 A1 | 5/2002 | Cofano et al. | |
| 2002/0063726 A1 | 5/2002 | Jouppi | |
| 2002/0073429 A1 | 6/2002 | Beane et al. | |
| 2002/0082498 A1 | 6/2002 | Wendt et al. | |
| 2002/0085030 A1 | 7/2002 | Ghani | |
| 2002/0095238 A1 | 7/2002 | Ahlin et al. | |
| 2002/0095239 A1 | 7/2002 | Wallach et al. | |
| 2002/0098879 A1 | 7/2002 | Rheey | |
| 2002/0104094 A1 | 8/2002 | Alexander et al. | |
| 2002/0106998 A1 | 8/2002 | Presley et al. | |
| 2002/0109770 A1 | 8/2002 | Terada | |
| 2002/0109775 A1 | 8/2002 | White et al. | |
| 2002/0111988 A1 | 8/2002 | Sato | |
| 2002/0120362 A1 | 8/2002 | Lathan et al. | |
| 2002/0123941 A1 | 9/2002 | Donahue et al. | |
| 2002/0128985 A1 | 9/2002 | Greenwald | |
| 2002/0130950 A1 | 9/2002 | James et al. | |
| 2002/0133062 A1 | 9/2002 | Arling et al. | |
| 2002/0141595 A1 | 10/2002 | Jouppi | |
| 2002/0143923 A1 | 10/2002 | Alexander | |
| 2002/0177925 A1 | 11/2002 | Onishi et al. | |
| 2002/0183598 A1 | 12/2002 | Teraura et al. | |
| 2002/0183894 A1 | 12/2002 | Wang et al. | |
| 2002/0184674 A1 | 12/2002 | Xi et al. | |
| 2002/0186243 A1 | 12/2002 | Ellis et al. | |
| 2002/0193908 A1 | 12/2002 | Parker et al. | |
| 2003/0021107 A1 | 1/2003 | Howell et al. | |
| 2003/0030397 A1 | 2/2003 | Simmons | |
| 2003/0048481 A1 | 3/2003 | Kobayashi et al. | |
| 2003/0050733 A1 | 3/2003 | Wang et al. | |
| 2003/0050734 A1 | 3/2003 | Lapham | |
| 2003/0052993 A1 | 3/2003 | Zadok | |
| 2003/0060808 A1 | 3/2003 | Wilk | |
| 2003/0063600 A1 | 4/2003 | Noma et al. | |
| 2003/0065731 A1 | 4/2003 | Mohammed et al. | |
| 2003/0069752 A1 | 4/2003 | Ledain et al. | |
| 2003/0069828 A1 | 4/2003 | Blazey et al. | |
| 2003/0080901 A1 | 5/2003 | Piotrowski | |
| 2003/0100892 A1 | 5/2003 | Morley et al. | |
| 2003/0104806 A1 | 6/2003 | Ruef et al. | |
| 2003/0112823 A1 | 6/2003 | Collins et al. | |
| 2003/0114962 A1 | 6/2003 | Niemeyer | |
| 2003/0120714 A1 | 6/2003 | Wolff et al. | |
| 2003/0126361 A1 | 7/2003 | Slater et al. | |
| 2003/0135097 A1 | 7/2003 | Wiederhold et al. | |
| 2003/0135203 A1 | 7/2003 | Wang et al. | |
| 2003/0144579 A1 | 7/2003 | Buss | |
| 2003/0144649 A1 | 7/2003 | Ghodoussi et al. | |
| 2003/0144768 A1 * | 7/2003 | Hennion | A61B 34/35 |
| | | | 701/2 |
| 2003/0151658 A1 | 8/2003 | Smith | |
| 2003/0152145 A1 | 8/2003 | Kawakita | |
| 2003/0171710 A1 | 9/2003 | Bassuk et al. | |
| 2003/0174285 A1 | 9/2003 | Trumbull | |
| 2003/0180697 A1 | 9/2003 | Kim et al. | |
| 2003/0195662 A1 | 10/2003 | Wang et al. | |
| 2003/0199000 A1 | 10/2003 | Valkirs et al. | |
| 2003/0206242 A1 | 11/2003 | Choi | |
| 2003/0212472 A1 | 11/2003 | Mckee | |
| 2003/0216833 A1 | 11/2003 | Mukai et al. | |
| 2003/0216834 A1 | 11/2003 | Allard | |
| 2003/0220541 A1 | 11/2003 | Salisbury et al. | |
| 2003/0220715 A1 | 11/2003 | Kneifel et al. | |
| 2003/0231244 A1 | 12/2003 | Bonilla et al. | |
| 2003/0232649 A1 | 12/2003 | Gizis et al. | |
| 2003/0236590 A1 | 12/2003 | Park et al. | |
| 2004/0001197 A1 | 1/2004 | Ko et al. | |
| 2004/0001676 A1 | 1/2004 | Colgan et al. | |
| 2004/0008138 A1 | 1/2004 | Hockley et al. | |
| 2004/0010344 A1 | 1/2004 | Hiratsuka et al. | |
| 2004/0012362 A1 | 1/2004 | Tsurumi | |
| 2004/0013295 A1 | 1/2004 | Sabe et al. | |
| 2004/0017475 A1 | 1/2004 | Akers et al. | |
| 2004/0019406 A1 | 1/2004 | Wang et al. | |
| 2004/0024490 A1 | 2/2004 | Mclurkin et al. | |
| 2004/0041904 A1 | 3/2004 | Lapalme et al. | |
| 2004/0048633 A1 | 3/2004 | Sato et al. | |
| 2004/0065073 A1 | 4/2004 | Nash | |
| 2004/0068657 A1 | 4/2004 | Alexander et al. | |
| 2004/0078219 A1 | 4/2004 | Kaylor et al. | |
| 2004/0080610 A1 | 4/2004 | James et al. | |
| 2004/0088077 A1 | 5/2004 | Jouppi et al. | |
| 2004/0088078 A1 | 5/2004 | Jouppi et al. | |
| 2004/0093409 A1 | 5/2004 | Thompson et al. | |
| 2004/0095516 A1 | 5/2004 | Rohlicek | |
| 2004/0098167 A1 | 5/2004 | Yi et al. | |
| 2004/0102167 A1 | 5/2004 | Shim et al. | |
| 2004/0107254 A1 | 6/2004 | Ludwig et al. | |
| 2004/0107255 A1 | 6/2004 | Ludwig et al. | |
| 2004/0117065 A1 | 6/2004 | Wang et al. | |
| 2004/0117067 A1 | 6/2004 | Jouppi | |
| 2004/0123158 A1 | 6/2004 | Roskind | |
| 2004/0135879 A1 | 7/2004 | Stacy et al. | |
| 2004/0138547 A1 | 7/2004 | Wang et al. | |
| 2004/0140404 A1 | 7/2004 | Ohta et al. | |
| 2004/0143421 A1 | 7/2004 | Wang et al. | |
| 2004/0148638 A1 | 7/2004 | Weisman et al. | |
| 2004/0150725 A1 | 8/2004 | Taguchi | |
| 2004/0153211 A1 | 8/2004 | Kamoto et al. | |
| 2004/0157612 A1 | 8/2004 | Kim | |
| 2004/0162637 A1 | 8/2004 | Wang et al. | |
| 2004/0167666 A1 | 8/2004 | Wang et al. | |
| 2004/0167668 A1 | 8/2004 | Wang et al. | |
| 2004/0168148 A1 | 8/2004 | Goncalves et al. | |
| 2004/0170300 A1 | 9/2004 | Jouppi | |
| 2004/0172301 A1 | 9/2004 | Mihai et al. | |
| 2004/0172306 A1 | 9/2004 | Wohl et al. | |
| 2004/0174129 A1 | 9/2004 | Wang et al. | |
| 2004/0175684 A1 | 9/2004 | Kaasa et al. | |
| 2004/0179714 A1 | 9/2004 | Jouppi | |
| 2004/0186623 A1 | 9/2004 | Dooley et al. | |

(56) References Cited

U.S. PATENT DOCUMENTS

| | | |
|---|---|---|
| 2004/0189700 A1 | 9/2004 | Mandavilli et al. |
| 2004/0201602 A1 | 10/2004 | Mody et al. |
| 2004/0202281 A1 | 10/2004 | Colbeth et al. |
| 2004/0205664 A1 | 10/2004 | Prendergast |
| 2004/0215490 A1 | 10/2004 | Duchon et al. |
| 2004/0218099 A1 | 11/2004 | Washington |
| 2004/0222638 A1 | 11/2004 | Bednyak |
| 2004/0224676 A1 | 11/2004 | Iseki |
| 2004/0230340 A1 | 11/2004 | Fukuchi et al. |
| 2004/0240981 A1 | 12/2004 | Dothan et al. |
| 2004/0241981 A1 | 12/2004 | Doris et al. |
| 2004/0243147 A1 | 12/2004 | Lipow |
| 2004/0243712 A1 | 12/2004 | Sakai et al. |
| 2004/0260790 A1 | 12/2004 | Balloni et al. |
| 2005/0003330 A1 | 1/2005 | Asgarinejad et al. |
| 2005/0004708 A1 | 1/2005 | Goldenberg et al. |
| 2005/0007445 A1* | 1/2005 | Foote .................. H04N 7/142 348/E7.079 |
| 2005/0013149 A1 | 1/2005 | Trossell |
| 2005/0021182 A1 | 1/2005 | Wang et al. |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka et al. |
| 2005/0065813 A1 | 3/2005 | Mishelevich et al. |
| 2005/0068294 A1* | 3/2005 | Cheng .................. G06F 3/011 345/161 |
| 2005/0071046 A1 | 3/2005 | Miyazaki et al. |
| 2005/0073575 A1 | 4/2005 | Thacher et al. |
| 2005/0075544 A1 | 4/2005 | Shapiro et al. |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovyrin et al. |
| 2005/0110867 A1* | 5/2005 | Schulz .................. H04N 7/142 348/E7.083 |
| 2005/0122390 A1 | 6/2005 | Wang et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | Mcgee et al. |
| 2005/0264648 A1 | 12/2005 | Ivashin et al. |
| 2005/0264649 A1 | 12/2005 | Chang et al. |
| 2005/0267826 A1 | 12/2005 | Levy et al. |
| 2005/0283414 A1 | 12/2005 | Fernandes et al. |
| 2005/0286759 A1 | 12/2005 | Zitnick et al. |
| 2006/0007943 A1 | 1/2006 | Fellman |
| 2006/0010028 A1 | 1/2006 | Sorensen |
| 2006/0013263 A1 | 1/2006 | Fellman |
| 2006/0013469 A1 | 1/2006 | Wang et al. |
| 2006/0013488 A1 | 1/2006 | Inoue |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |
| 2006/0048286 A1 | 3/2006 | Donato |
| 2006/0052676 A1 | 3/2006 | Wang et al. |
| 2006/0052684 A1 | 3/2006 | Takahashi et al. |
| 2006/0056655 A1 | 3/2006 | Wen et al. |
| 2006/0056837 A1 | 3/2006 | Vapaakoski |
| 2006/0064212 A1 | 3/2006 | Thorne |
| 2006/0066609 A1 | 3/2006 | Iodice et al. |
| 2006/0071797 A1 | 4/2006 | Rosenfeld et al. |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0119701 A1* | 6/2006 | King .................. A61B 90/361 348/E7.086 |
| 2006/0122482 A1 | 6/2006 | Mariotti et al. |
| 2006/0125356 A1 | 6/2006 | Meek et al. |
| 2006/0142983 A1 | 6/2006 | Sorensen et al. |
| 2006/0149418 A1 | 7/2006 | Anvari |
| 2006/0161136 A1 | 7/2006 | Anderson et al. |
| 2006/0161303 A1 | 7/2006 | Wang et al. |
| 2006/0164546 A1 | 7/2006 | Adachi |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178559 A1 | 8/2006 | Kumar et al. |
| 2006/0178776 A1 | 8/2006 | Feingold et al. |
| 2006/0178777 A1 | 8/2006 | Park et al. |
| 2006/0189393 A1 | 8/2006 | Edery |
| 2006/0195569 A1 | 8/2006 | Barker |
| 2006/0224781 A1 | 10/2006 | Tsao et al. |
| 2006/0238379 A1 | 10/2006 | Kimchi et al. |
| 2006/0247045 A1 | 11/2006 | Jeong et al. |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0016328 A1 | 1/2007 | Ziegler et al. |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0057866 A1 | 3/2007 | Lee et al. |
| 2007/0061041 A1 | 3/2007 | Zweig |
| 2007/0064092 A1 | 3/2007 | Sandbeg et al. |
| 2007/0067734 A1 | 3/2007 | Cunningham et al. |
| 2007/0078566 A1 | 4/2007 | Wang et al. |
| 2007/0093279 A1 | 4/2007 | Janik |
| 2007/0112700 A1 | 5/2007 | Den haan et al. |
| 2007/0116152 A1 | 5/2007 | Thesling |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0170886 A1 | 7/2007 | Plishner |
| 2007/0176060 A1 | 8/2007 | White et al. |
| 2007/0182811 A1 | 8/2007 | Rockefeller et al. |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0226949 A1 | 10/2007 | Hahm et al. |
| 2007/0250212 A1 | 10/2007 | Halloran et al. |
| 2007/0254631 A1 | 11/2007 | Spooner |

(56) References Cited

U.S. PATENT DOCUMENTS

| | | |
|---|---|---|
| 2007/0255706 A1 | 11/2007 | Iketani et al. |
| 2007/0262884 A1 | 11/2007 | Goncalves et al. |
| 2007/0273751 A1 | 11/2007 | Sachau |
| 2007/0290040 A1 | 12/2007 | Wurman et al. |
| 2007/0291109 A1 | 12/2007 | Wang et al. |
| 2007/0291128 A1 | 12/2007 | Wang et al. |
| 2008/0009969 A1 | 1/2008 | Bruemmer et al. |
| 2008/0011904 A1 | 1/2008 | Cepollina et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D'andrea et al. |
| 2008/0065268 A1 | 3/2008 | Wang et al. |
| 2008/0082211 A1 | 4/2008 | Wang et al. |
| 2008/0086241 A1 | 4/2008 | Phillips et al. |
| 2008/0091340 A1 | 4/2008 | Milstein et al. |
| 2008/0126132 A1 | 5/2008 | Warner et al. |
| 2008/0133052 A1 | 6/2008 | Jones et al. |
| 2008/0161969 A1 | 7/2008 | Lee et al. |
| 2008/0174570 A1 | 7/2008 | Jobs et al. |
| 2008/0201016 A1 | 8/2008 | Finlay |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0232763 A1 | 9/2008 | Brady |
| 2008/0255703 A1 | 10/2008 | Wang et al. |
| 2008/0263451 A1 | 10/2008 | Portele et al. |
| 2008/0263628 A1 | 10/2008 | Norman et al. |
| 2008/0267069 A1 | 10/2008 | Thielman et al. |
| 2008/0269949 A1 | 10/2008 | Norman et al. |
| 2008/0281467 A1 | 11/2008 | Pinter |
| 2008/0285886 A1 | 11/2008 | Allen |
| 2008/0306375 A1 | 12/2008 | Sayler et al. |
| 2009/0021572 A1 | 1/2009 | Garudadri et al. |
| 2009/0030552 A1 | 1/2009 | Nakadai et al. |
| 2009/0044334 A1 | 2/2009 | Parsell et al. |
| 2009/0049640 A1 | 2/2009 | Lee et al. |
| 2009/0055023 A1 | 2/2009 | Walters et al. |
| 2009/0070135 A1 | 3/2009 | Parida et al. |
| 2009/0086013 A1 | 4/2009 | Thapa |
| 2009/0102919 A1 | 4/2009 | Zamierowski et al. |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0144425 A1 | 6/2009 | Marr et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0173846 A1 | 7/2009 | Katz |
| 2009/0177323 A1 | 7/2009 | Ziegler et al. |
| 2009/0177641 A1 | 7/2009 | Raghavan |
| 2009/0185792 A1 | 7/2009 | Braunstein et al. |
| 2009/0234499 A1 | 9/2009 | Nielsen et al. |
| 2009/0237317 A1 | 9/2009 | Rofougaran |
| 2009/0240371 A1 | 9/2009 | Wang et al. |
| 2009/0247136 A1 | 10/2009 | Srinivasan et al. |
| 2009/0248041 A1 | 10/2009 | Williams et al. |
| 2009/0248200 A1 | 10/2009 | Root |
| 2009/0259339 A1 | 10/2009 | Wright et al. |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |
| 2010/0030578 A1 | 2/2010 | Siddique et al. |
| 2010/0051596 A1 | 3/2010 | Diedrick et al. |
| 2010/0063848 A1 | 3/2010 | Kremer et al. |
| 2010/0066804 A1 | 3/2010 | Shoemake et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0081430 A1 | 4/2010 | Rofougaran |
| 2010/0085874 A1 | 4/2010 | Noy et al. |
| 2010/0088232 A1 | 4/2010 | Gale |
| 2010/0100240 A1 | 4/2010 | Wang et al. |
| 2010/0115418 A1 | 5/2010 | Wang et al. |
| 2010/0116566 A1 | 5/2010 | Ohm et al. |
| 2010/0131103 A1 | 5/2010 | Herzog et al. |
| 2010/0145479 A1 | 6/2010 | Griffiths |
| 2010/0157825 A1 | 6/2010 | Anderlind et al. |
| 2010/0171826 A1 | 7/2010 | Hamilton et al. |
| 2010/0191375 A1 | 7/2010 | Wright et al. |
| 2010/0228249 A1 | 9/2010 | Mohr et al. |
| 2010/0238194 A1 | 9/2010 | Roach, Jr. |
| 2010/0268383 A1 | 10/2010 | Wang et al. |
| 2010/0278086 A1 | 11/2010 | Pochiraju et al. |
| 2010/0286905 A1 | 11/2010 | Goncalves et al. |
| 2010/0301679 A1 | 12/2010 | Murray et al. |
| 2010/0323783 A1 | 12/2010 | Nonaka et al. |
| 2011/0022705 A1 | 1/2011 | Yellamraju et al. |
| 2011/0050841 A1 | 3/2011 | Wang et al. |
| 2011/0066262 A1 | 3/2011 | Kelly et al. |
| 2011/0071675 A1 | 3/2011 | Wells et al. |
| 2011/0071702 A1 | 3/2011 | Wang et al. |
| 2011/0072114 A1 | 3/2011 | Hoffert et al. |
| 2011/0118748 A1 | 5/2011 | Itkowitz |
| 2011/0153198 A1 | 6/2011 | Kokkas et al. |
| 2011/0169832 A1 | 7/2011 | Brown et al. |
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0193949 A1 | 8/2011 | Nambakam et al. |
| 2011/0195701 A1 | 8/2011 | Cook et al. |
| 2011/0213210 A1 | 9/2011 | Temby et al. |
| 2011/0218674 A1 | 9/2011 | Stuart et al. |
| 2011/0244928 A1 | 10/2011 | Cherpes et al. |
| 2011/0245973 A1 | 10/2011 | Wang et al. |
| 2011/0249079 A1 | 10/2011 | Santamaria et al. |
| 2011/0280551 A1 | 11/2011 | Sammon |
| 2011/0288417 A1 | 11/2011 | Pinter et al. |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0023506 A1 | 1/2012 | Maeckel et al. |
| 2012/0036484 A1 | 2/2012 | Zhang et al. |
| 2012/0059946 A1 | 3/2012 | Wang |
| 2012/0072023 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0113856 A1 | 5/2012 | Krishnaswamy |
| 2012/0136371 A1 | 5/2012 | Mendez |
| 2012/0182392 A1 | 7/2012 | Kearns et al. |
| 2012/0191246 A1 | 7/2012 | Roe et al. |
| 2012/0191464 A1 | 7/2012 | Stuart et al. |
| 2012/0203731 A1 | 8/2012 | Nelson et al. |
| 2012/0215380 A1 | 8/2012 | Fouillade et al. |
| 2012/0218374 A1 | 8/2012 | Matula et al. |
| 2012/0220372 A1 | 8/2012 | Cheung et al. |
| 2012/0242279 A1 | 9/2012 | Tso et al. |
| 2012/0291809 A1 | 11/2012 | Kuhe et al. |
| 2013/0035138 A1 | 2/2013 | Abbott |
| 2013/0158720 A1 | 6/2013 | Zywicki et al. |
| 2013/0250938 A1 | 9/2013 | Anandakumar et al. |
| 2013/0321257 A1 | 12/2013 | Moore et al. |
| 2014/0015914 A1 | 1/2014 | Delaunay |
| 2014/0032244 A1 | 1/2014 | Kolls et al. |
| 2014/0047022 A1 | 2/2014 | Chan et al. |
| 2014/0085543 A1 | 3/2014 | Hartley et al. |
| 2014/0135990 A1 | 5/2014 | Stuart et al. |
| 2014/0139616 A1* | 5/2014 | Pinter ................ A61B 5/02055 348/14.08 |
| 2014/0155755 A1 | 6/2014 | Pinter et al. |
| 2014/0250191 A1 | 9/2014 | Altman et al. |
| 2014/0267552 A1 | 9/2014 | Wang et al. |
| 2014/0347269 A1 | 11/2014 | Ballantyne et al. |
| 2015/0119652 A1 | 4/2015 | Hyde et al. |
| 2015/0190927 A1 | 7/2015 | Sutherland et al. |
| 2015/0286789 A1 | 10/2015 | Stuart et al. |
| 2016/0047903 A1 | 2/2016 | Dussan |
| 2017/0015003 A1 | 1/2017 | Sutherland et al. |

(56) References Cited

U.S. PATENT DOCUMENTS

| | | | |
|---|---|---|---|
| 2017/0195623 A1 | 7/2017 | Stuart et al. | |
| 2017/0322718 A1 | 11/2017 | Ballantyne et al. | |
| 2017/0357263 A1 | 12/2017 | Glatfelter et al. | |

FOREIGN PATENT DOCUMENTS

| | | |
|---|---|---|
| CN | 1404695 A | 3/2003 |
| CN | 1554193 A | 12/2004 |
| CN | 1554985 A | 12/2004 |
| CN | 1561923 A | 1/2005 |
| CN | 1743144 A | 3/2006 |
| CN | 101049017 A | 10/2007 |
| CN | 101106939 A | 1/2008 |
| CN | 101151614 A | 3/2008 |
| CN | 100407729 C | 7/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 466492 A2 | 1/1992 |
| EP | 488673 A2 | 6/1992 |
| EP | 0981905 B1 | 1/2002 |
| EP | 1262142 A2 | 12/2002 |
| EP | 1304872 A1 | 4/2003 |
| EP | 1536660 A2 | 6/2005 |
| EP | 1573406 A2 | 9/2005 |
| EP | 1594660 A2 | 11/2005 |
| EP | 1763243 A2 | 3/2007 |
| EP | 1791464 A2 | 6/2007 |
| EP | 1800476 A2 | 6/2007 |
| EP | 1819108 A2 | 8/2007 |
| EP | 1856644 A2 | 11/2007 |
| EP | 1536660 A3 | 4/2008 |
| EP | 1928310 A2 | 6/2008 |
| EP | 1232610 B1 | 1/2009 |
| EP | 2027716 A2 | 2/2009 |
| EP | 2145274 A1 | 1/2010 |
| EP | 2214111 A2 | 8/2010 |
| EP | 2263158 A2 | 12/2010 |
| EP | 2300930 A1 | 3/2011 |
| EP | 2342651 A1 | 7/2011 |
| EP | 2542178 A2 | 1/2013 |
| EP | 2300930 B1 | 7/2015 |
| GB | 2431261 A | 4/2007 |
| JP | H07-194609 A | 8/1995 |
| JP | H07-213753 A | 8/1995 |
| JP | H07-248823 A | 9/1995 |
| JP | H07-257422 A | 10/1995 |
| JP | H08-84328 A | 3/1996 |
| JP | 8320727 A | 12/1996 |
| JP | H08-320727 A | 12/1996 |
| JP | 9267276 A | 10/1997 |
| JP | H09-267276 A | 10/1997 |
| JP | H10-79097 A | 3/1998 |
| JP | H10-288689 A | 10/1998 |
| JP | H11-220706 A | 8/1999 |
| JP | 2000-032319 A | 1/2000 |
| JP | 2000-049800 A | 2/2000 |
| JP | 2000-079587 A | 3/2000 |
| JP | 2000-196876 A | 7/2000 |
| JP | 2000196876 A | 7/2000 |
| JP | 2001-125641 A | 5/2001 |
| JP | 2001-147718 A | 5/2001 |
| JP | 2001147718 A | 5/2001 |
| JP | 2001-179663 A | 7/2001 |
| JP | 2001-188124 A | 7/2001 |
| JP | 2001-198865 A | 7/2001 |
| JP | 2001-198868 A | 7/2001 |
| JP | 2001-199356 A | 7/2001 |
| JP | 2001188124 A | 7/2001 |
| JP | 2001198865 A | 7/2001 |
| JP | 2001198868 A | 7/2001 |
| JP | 2001199356 A | 7/2001 |
| JP | 2002-000574 A | 1/2002 |
| JP | 2002000574 A | 1/2002 |
| JP | 2002-046088 A | 2/2002 |
| JP | 2002046088 A | 2/2002 |
| JP | 2002-101333 A | 4/2002 |
| JP | 2002-112970 A | 4/2002 |
| JP | 2002-235423 A | 8/2002 |
| JP | 2002235423 A | 8/2002 |
| JP | 2002-305743 A | 10/2002 |
| JP | 2002305743 A | 10/2002 |
| JP | 2002-321180 A | 11/2002 |
| JP | 2002-355779 A | 12/2002 |
| JP | 2002355779 A | 12/2002 |
| JP | 2004-181229 A | 7/2004 |
| JP | 2004-524824 T | 8/2004 |
| JP | 2004-261941 A | 9/2004 |
| JP | 2004-289379 A | 10/2004 |
| JP | 2005-028066 A | 2/2005 |
| JP | 2005028066 A | 2/2005 |
| JP | 2005-059170 A | 3/2005 |
| JP | 2005-111083 A | 4/2005 |
| JP | 2006-508806 A | 3/2006 |
| JP | 2006-109094 A | 4/2006 |
| JP | 2006-224294 A | 8/2006 |
| JP | 2006-246438 A | 9/2006 |
| JP | 2007-007040 A | 1/2007 |
| JP | 2007-081646 A | 3/2007 |
| JP | 2007082223 A | 3/2007 |
| JP | 2007-232208 A | 9/2007 |
| JP | 2007-316966 A | 12/2007 |
| JP | 2008538301 A | 10/2008 |
| JP | 2009-125133 A | 6/2009 |
| JP | 2010-064154 A | 3/2010 |
| JP | 2010-532109 A | 9/2010 |
| JP | 2010532109 A | 9/2010 |
| JP | 2010-246954 A | 11/2010 |
| KR | 20000035050 A | 6/2000 |
| KR | 10-2006-0037979 A | 5/2006 |
| KR | 10-2009-0012542 A | 2/2009 |
| KR | 10-2010-0019479 A | 2/2010 |
| KR | 10-2010-0139037 A | 12/2010 |
| WO | 93/06690 A1 | 4/1993 |
| WO | 97/42761 A1 | 11/1997 |
| WO | 1998/51078 A1 | 11/1998 |
| WO | 99/67067 A1 | 12/1999 |
| WO | 2000/025516 A1 | 5/2000 |
| WO | 2000/033726 A1 | 6/2000 |
| WO | 01/31861 A1 | 5/2001 |
| WO | 2003/077745 A1 | 9/2003 |
| WO | 2004/008738 A1 | 1/2004 |
| WO | 2004/012018 A2 | 2/2004 |
| WO | 2004/075456 A2 | 9/2004 |
| WO | 2006/012797 A1 | 2/2006 |
| WO | 2006/044847 A2 | 4/2006 |
| WO | 2006/078611 A2 | 7/2006 |
| WO | 2007/041038 A3 | 4/2007 |
| WO | 2007/041295 A2 | 4/2007 |
| WO | 2008/100272 A2 | 8/2008 |
| WO | 2008/100272 A3 | 10/2008 |
| WO | 2009/117274 A2 | 9/2009 |
| WO | 2009/128997 A1 | 10/2009 |
| WO | 2009/145958 A2 | 12/2009 |
| WO | 2010/006205 A1 | 1/2010 |
| WO | 2010/006211 A1 | 1/2010 |
| WO | 2010/033666 A1 | 3/2010 |
| WO | 2010/047881 A1 | 4/2010 |
| WO | 2010/062798 A1 | 6/2010 |
| WO | 2010/065257 A1 | 6/2010 |
| WO | 2010/120407 A1 | 10/2010 |
| WO | 2011/028589 A2 | 3/2011 |
| WO | 2011/028589 A3 | 4/2011 |
| WO | 2011/097130 A2 | 8/2011 |
| WO | 2011/097132 A2 | 8/2011 |
| WO | 2011/109336 A2 | 9/2011 |
| WO | 2011/097132 A3 | 12/2011 |
| WO | 2011/149902 A2 | 12/2011 |

(56) References Cited

FOREIGN PATENT DOCUMENTS

| WO | 2011/109336 A3 | 1/2012 |
|---|---|---|
| WO | 2013/097264 A1 | 7/2013 |

OTHER PUBLICATIONS

Appeal from the U.S District Court for the Central District of California in case No. 11-cv-9185, Judge Percy Anderson, Joint Appendix, vol. I of IV, Jun. 24, 2013, pp. A1-A6357.
Appeal from the U.S District Court for the Central District of California in case No. 11-cv-9185, Judge Percy Anderson, Joint Appendix, vol. II of IV, Jun. 24, 2013, pp. A6849-A10634.
Appeal from the U.S District Court for the Central District of California in case No. 11-cv-9185, Judge Percy Anderson, Joint Appendix, vol. III of IV, Jun. 24, 2013, pp. A10654-A15517.
Appeal from the U.S District Court for the Central District of California in case No. 11-cv-9185, Judge Percy Anderson, Joint Appendix, vol. IV of IV, Jun. 24, 2013, pp. A15677-A18127.
Appeal from the U.S District Court for the Central District of California in No. 11-CV-9185, Judge Percy Anderson, May 9, 2014, pp. 1-48.
Civil Minutes—General: Case No. CV 11-9185PA (AJWx), *InTouch Tech., Inc.* v. *VGO Commons, Inc.*, Sep. 10, 2012, 7 pages.
Defendant VGO Communications, Inc.'s Invalidity Contentions Pursuant to the Feb. 27, 2012 Civil Minute Order, May 2, 2012, 143 pages.
Defendant—Counterclaimant VGO Communications, Inc.'s Supplemental Invalidity Contentions Pursuant to the Feb. 27, 2012 Civil Minute Order, May 14, 2012, 228 pages.
"Google translation of: Innovations Report", From research project to television star: Care-O-bot in ZDF series, available online at <http://www.innovations-report.de/specials/printa.php?id=5157>, Sep. 28, 2001, 2 pages.
"Magne Charge", Smart Power for Electric Vehicles, Aug. 26, 1997, 2 pages.
"More Online Robots: Robots that Manipulate", available online at <http://ford.ieor.berkeley.edu/ir/robots_a2.html>, Retrieved on Nov. 23, 2010, Aug. 2001, 2 pages.
"MPEG File Format Summary", available online at <http://www.fileformat.info/format/mpeg/egff.htm>, Feb. 1, 2001, 7 pages.
"Nomad Scout Language Reference Manual", Nomadic Technologies, Software Version 2.7, Part No. DOC00002, Jul. 12, 1999, 47 pages.
"Nomad Scout User's Manual", Nomadic Technologies, Software Version 2. 7, Part No. DOC00004, Jul. 12, 1999, pp. 1-59.
Opening Brief for Plaintiff—Appellant InTouch Technologies, Inc., Appeal from the U.S. District Court for the Central District of California in Case No. 11-cv-9185, Judge Percy Anderson, Apr. 12, 2013, 187 pages.
PictureTel Adds New Features and Functionality to Its Award-Winning Live200 Desktop Videoconferencing System, PR Newswire Association, LLC, Gale, Cengage Learning, Jun. 13, 1997, 4 pages.
Reply Brief for Defendant—Appellee VGO Communications, Inc., Appeal from the U.S. District Court for the Central District of California, in Case No. 2:11-cv-9185, Judge Percy Anderson, May 28, 2013, 75 pages.
Reply Brief for Plaintiff—Appellant InTouch Technologies, Inc., Appeal from the U.S. District Court for the Central District of California in Case No. 11-cv-9185, Judge Percy Anderson, Jun. 14, 2013, 39 pages.
"Robart I, II, III", Spawar, Systems Center Pacific, 1998, 8 pages.
Using your Infrared Cell Phone Camera, available online at <http://www.catsdomain.com/xray/about.htm>, Courtesy of Internet Wayback Machine, Jan. 30, 2010, 4 pages.
Ivanova, Natali, "Master's Thesis: Internet Based Interface for Control of a Mobile Robot", Department of Numerical Analysis and Computer Science, 2003, 59 pages.
Jacobs et al., "Applying Telemedicine to Outpatient Physical Therapy", AMIA, Annual Symposium Proceedings, 2002, 1 page.

Jenkins et al., "Telehealth Advancing Nursing Practice", Nursing Outlook, vol. 49, No. 2, Mar. 2001, pp. 100-105.
Johanson, Mathias, "Supporting Video-Mediated Communication Over the Internet", Depailment of Computer Engineering, Chalmers University of Technology, Gothenburg, Sweden, 2003, 222 pages.
ACM Digital Library Record, "Autonomous Robots vol. 11 Issue 1", available online at <http://dl.acm.org/citation.cfm?id=591550&picked=prox&cfid=360891374&cftoken=35225929>, Jul. 2001, 2 pages.
Active Media, Inc., "Saphira Software Manual", Saphira Version 5.3, 1997, 105 pages.
Activmedia Robotics, "Pioneer 2/PeopleBot TM", Operations Manual, Version 9, Oct. 2001, 78 pages.
Adams, Chris, "Simulation of Adaptive Behavior (SAB'02)", Mobile Robotics Research Group, The Seventh International Conference, retrieved on Jan. 22, 2014, available online at <http://www.dai.ed.ac.uk/groups/mrg/MRG.html>, Aug. 4-11, 2002, 1 page.
Ando et al., "A Multimedia Self-service Terminal with Conferencing Functions", Robot and Human Communication, Tokyo, Proceedings of 4th IEEE International Workshop, Jul. 5-7, 1995, pp. 357-362.
Android Amusement Corp., "What Marketing Secret Renting Robots from Android Amusement Corp!", (Advertisement), 1982, 1 page.
Apple Inc., "I Phone", iPhone Series, XP002696350, Sep. 21, 2012, pp. 1-29.
Applebome, Peter, "Planning Domesticated Robots for Tomorrow's Household", New York Times, available online at <http://www.theoldrobots.com/images17/dc17.jpg>, Mar. 4, 1982, pp. 21 and 23.
Bar-Cohen et al., "Virtual Reality Robotic Telesurgery Simulations Using MEMICA Haptic System", Proceedings of SPIE's 8th Annual International Symposium on Smart Structures and Materials, Mar. 5-8, 2001, pp. 1-7.
Barrett, Rick, "Video Conferencing Business Soars as Companies Cut Travel; Some Travel Cuts Are Permanent", available online at <http://www.ivci.com/international_videoconferencing_news_videoconferencing_news_19.html>, May 13, 2002, 2 pages.
Bartholomew, "Pharmacy Apothecary", available online at <http://classes.bnf.fr/ema/grands/034.htm>, retrieved on Jul. 26, 2012, 2 pages.
Bauer et al., "Remote Telesurgical Mentoring: Feasibility and Efficacy", IEEE, Proceedings of the 33rd Hawaii International Conference on System Sciences, 2000, pp. 1-9.
Bauer, Jeffrey C., "Service Robots in Health Care: The Evolution of Mechanical Solutions to Human Resource Problems", Bon Secours Health System Inc., Technology Early Warning System(TEWS), Future of Service Robots in Health Care, Jun. 2003, pp. 1-10.
Bischoff, Rainer, "Design Concept and Realization of the Humanoid Service Robot HERMES", Field and Service Robotics, Springer, 1998, pp. 485-492.
Blackwell, Gerry, "Video: A Wireless LAN Killer App?", available online at <http://www.wi-fiplanet.com/columns/article.php/1010261/Video-A-Wireless-LAN-Killer>, Apr. 16, 2002, 4 pages.
Blaer et al., "TopBot: Automated Network Topology Detection With a Mobile Robot", IEEE, Proceedings of the 2003 International Conference on Robotics 7 Automation, Taipei, Taiwan, Sep. 14-19, 2003, pp. 1582-1587.
Bradner, S., "The Internet Standards Process—Revision 3", Network Working Group, Request for Comments: 2026, BCP: 9, Obsoletes: 1602, Category: Best Current Practice, Oct. 1996, pp. 1-36.
Brenner, Pablo, "A technical tutorial on the IEEE 802.11 protocol", Breezecom Wireless Communications, 1997, pp. 1-24.
Breslow et al., "Effect of a Multiple-Site Intensive Care Unit Telemedicine Program on Clinical and Economic Outcome an Alternative Paradigm for Intensivist Staffing", Critical Care Med, vol. 32, No. 1, Jan. 2004, pp. 31-38.
Brooks, Rodney, "A Robust Layered Control System for a Mobile Robot", IEEE, Journal of Robotics and Automation, vol. 2, No. 1, Mar. 1986, pp. 14-23.
Brooks, Rodney Allen, "Remote Presence", Abstracts from Flesh & Machines, How Robots Will Change Us, Feb. 2002, pp. 131-147.
Celi et al., "The eICU: It's Not Just Telemedicine", Critical Care Medicine vol. 29, No. 8 (Supplement), Aug. 2001, pp. 183-189.

(56) References Cited

OTHER PUBLICATIONS

Cheetham et al., "Interface Development for a Child's Video Conferencing Robot", available online at <www.ryerson.ca/pebbles/publications/paper-iea200hfes-last.pdf>, 2000, 4 pages.
Christensen et al., "BeeSoft User's Guide and Reference", Robots for the Real World™, Real World Interface, Inc ., Sep. 26, 1997, 203 pages.
Chu et al., "Detection of Target Mobile Signal Strength", Technical Development, Motorola Inc, Jan. 1999, pp. 205-206.
Cleary et al., "State of the Ad in Surgical Robotics: Clinical Applications and Technology Challenges", Feb. 24, 2002, pp. 1-26.
CMU Course 16X62, "Robot user's manual", (describing the Nomad Scout), Carnegie Mellon University, Feb. 1, 2001, 11 pages.
CNN, "Floating 'Droids' to Roam Space Corridors of the Future", Available online at <http://edition.cnn.com/2000/TECH/space/01/12/psa/>, Jan. 12, 2000, 3 pages.
cnn.com, "Paging Dr.Robot: Machine Helps Doctors with Patients", Sep. 30, 2003, 3 pages.
Crowley, Susan L., "Hello to Our Future", AARP Bulletin, Jan. 2000, 12 pages.
Dalton, Barnaby, "Techniques for Web Telerobotics", PhD Thesis, University of Western Australia, 2001, 243 pages.
Dario et al., "A Robot Workstation for Diagnosis and Physical Therapy", IEEE Catalog No. 88TH0234-5, 1989, pp. 67-72.
Davies, Brian, "Robotics in Minimally Invasive Surgery", IEE Colloquium on Through the Keyhole: Microengineering in Minimally Invasive Surgery, 1995, pp. 1-2.
Davis, Erik, "Telefriend, Meet iRobot, The Smartest Webcam on Wheels", Wired Magazine, Issue 8.09, Available online at <http://www.wired.com/wired/archive/8.09/irobot.html?pg=1&topic=&topic_set=>, Sep. 2000, 3 pages.
Dean et al., "1992 AAAI Robot Exhibition and Competition", Articles, AI Magazine, vol. 14, No. 1, 1993, 15 pages.
Digiorgio, James, "Is Your Emergency Department of the 'Leading Edge?", Chicago Hospital News, vol. 2, No. 12, 2005, 3 pages.
Dudenhoeffer et al., "Command and Control Architectures for Autonomous Micro-Robotic Forces", FY00 Project Report, Idaho National Engineering and Environmental Laboratory Human Systems Engineering and Sciences Department, Idaho Falls, Apr. 2001, 43 pages.
Elhajj et al., "Real-Time Haptic Feedback in Internet-Based Telerobotic Operation", IEEE International Conference on Electro/Information Technology, available online at <http://www.egr.msu.edu/~ralab-web/cgi_bin/internet-teleoperation.php>, Jun. 2000, 10 pages.
Elhajj et al., "Supermedia in Internet-Based Telerobotic Operations", Management of Multimedia on the InternetLecture Notes in Computer Science, Springer-Verlag Berlin Heidelberg, vol. 2216, Oct. 29-Nov. 1, 2001, pp. 359-372.
Elhajj et al., "Synchronization and Control of Supermedia Transmission via the Internet", Proceedings of 2001 International Symposium on Intelligent Multimedia Video and Speech Processing, May 2-4, 2001, pp. 320-323.
Ellison et al., "Telerounding and Patient Satisfaction Following Surgery", vol. 199, No. 4, Oct. 2004, pp. 523-530.
Evans et al., "The Trackless Robotic Courier", PYXIS HelpMate®, 2007, 3 pages.
Fels et al., "Developing a Video-Mediated Communication System for Hospitalized Children", Telemedicine Journal, vol. 5, No. 2, 1999, 30 pages.
Fetterman et al., "Videoconferencing Over the Internet", 2001, 8 pages.
Fiorini et al., "Health Care Robotics: A Progress Report", IEEE International Conference on Robotics and Automation, Apr. 20-25, 1997, pp. 1271-1276.
Fong, Terrence, "Collaborative Control: A Robot-Centric Model for Vehicle Teleoperation", Doctoral Dissertation, Technical Report CMU-RI-TR-01-34, Robotics Institute, Carnegie Mellon University, Nov. 2001, 197 pages.
Fulbright et al., "SWAMI: An Autonomous Mobile Robot for Inspection of Nuclear Waste of Storage Facilities", Autonomous Robots, vol. 2, 1995, pp. 225-235.
Gaidioz et al., "Synchronizing Network Probes to Avoid Measurement Intrusiveness with the Network Weather Service", Proceedings of the Ninth International Symposium on High-Performance Distributed Computing, 2000, pp. 147-154.
Garner et al., "The Application of Telepresence in Medicine", BT Technology Journal, vol. 15, No. 4, Oct. 1, 1997, pp. 181-187.
Ghiasi et al., "A Generic Web-based Teleoperations Architecture: Details and Experience", Proceedings of SPIE, Telemanipulator and Telepresence Technologies VI, vol. 3840, No. 234, Sep. 19, 1999, 14 pages.
Goldberg et al., "Collaborative Teleoperation via the Internet", IEEE International Conference on Robotics and Automation (ICRA), vol. 2, 2000, pp. 2019-2024.
Goldberg et al., "Desktop Teleoperation via the World Wide Web", IEEE International Conference on Robotics and Automation, vol. 1, May 21-27, 1995, pp. 654-659.
Goldenberg et al., "Telemedicine in Otolaryngology", American Journal of Otolaryngology, vol. 23,No. 1, 2002, pp. 35-43.
Goldman, Lea, "Machine Dreams", available online at <http://www.forbes.com/global/2002/0527/043.html>, May 27, 2002, 5 pages.
Gostai, "Gostai Jazz: Robotic Telepresence", available online at <http://www.robotshop.com/media/files/pdf/gostai-iazz-information-sheet.pdf>, 4 pages.
Gump, Michael D., "Robot Technology Improves VA Pharmacies", U.S. Medicine Informational Central, Jul. 2001, 3 pages.
Al-Kassab et al., "A Review of Telemedicine", Journal of Telemedicine and Telecare, vol. 5, Supplement 1, 1999, pp. 103-106.
Han et al., "Construction of an Omnidirectional Mobile Robot Platform Based on Active Dual-Wheel Caster Mechanisms and Development of a Control Simulator", Journal of Intelligent and Robotic Systems, vol. 29, Issue 3, Nov. 2000, pp. 257-275.
Handley et al., "RFC 2327-SDP: Session Description Protocol", available online at <http://www.faqs.org/rfcs/rfc2327.html>, Apr. 1998, 22 pages.
Hanebeck et al., "ROMAN: A Mobile Robotic Assistant for Indoor Service Applications", IEEE/RSJ International Conference on Intelligent Robots and Systems, vol. 2, Sep. 7-11, 1997, pp. 518-525.
Harmo et al., "Moving Eye-Interactive Telepresence Over Internet With a Ball Shaped Mobile Robot", available online at <http://automation.tkk.fi/files/tervetaas/MovingEye4.pdf>, 2000, 6 pages.
Haule et al., "Control Scheme for Delayed Teleoperation Tasks", IEEE Pacific Rim Conference on Communications, Computers, and Signal Processing, May 17-19, 1995, pp. 157-160.
Hees, William P., "Communications Design fora Remote Presence Robot", CSCI E-131b, Final Project, Jan. 14, 2002, 12 pages.
Herias et al., "Flexible Virtual and Remote Laboratory for Teaching Robotics", Current Developments in Technology-Assisted Education, Jun. 2006, pp. 1959-1963.
Holmberg et al., "Development of a Holonomic Mobile Robot for Mobile Manipulation Tasks", International Journal of Robotics Research, vol. 19, No. 11, Nov. 2000, pp. 1066-1074.
Ishiguro et al., "Integrating a Perceptual Information Infrastructure with Robotic Avatars: A Framework for Tele-Existence", IEEE/RSJ International Conference on Intelligent Robots and Systems, vol. 2, 1999, pp. 1032-1038.
Ishihara et al., "Intelligent Microrobot DDS (Drug Delivery System) Measured and Controlled by Ultrasonics", Intelligent Robots and Systems '91. 'Intelligence for Mechanical Systems, IEEE/RSJ International Workshop, vol. 2, Nov. 3-5, 1991, pp. 1145-1150.
ITU, "Call Completion Supplementary Services for H.323", ITU-T, Telecommunication Standardization Sector of ITU, H.450.9, Series H: Audiovisual and Multimedia Systems, Nov. 2000, 63 pages.
ITU, "Call Intrusion Supplementary Service for H.323", ITU-T, Telecommunication Standardization Sector of ITU, H.450.11, Series H: Audiovisual and Multimedia Systems, Mar. 2001, 59 pages.
ITU, "Packet-Based Multimedia Communications Systems", ITU-T, Telecommunication Standardization Sector of ITU, H.323, Series H: Audiovisual and Multimedia Systems, Feb. 1998, 128 pages.

(56) References Cited

OTHER PUBLICATIONS

ITU, "Transmission of Non-Telephone Signals: A Far End Camera Control Protocol for Videoconferences Using H.224", ITU-T, Telecommunication Standardization Sector of ITU, H.281, Nov. 1994, 12 pages.
Paulos, Eric John, "Personal Tele-Embodiment", OskiCat Catalog Record, UCB Library Catalog, 2001, 3 pages.
Paulos et al., "Personal Tele-Embodiment", Chapter 9 in Goldberg, et al., ed. "Beyond webcams", MIT Press, Jan. 4, 2002, pp. 155-167.
Paulos, Eric John, "Personal Tele-Embodiment", Introductory and cover pages from 2001 Dissertation including Contents table, together with e-mails relating thereto from UC Berkeley Libraries, as shelved at UC Berkeley Engineering Library (Northern Regional library Facility), May 8, 2002, 25 pages (including 4 pages of e-mails).
Paulos et al., "PRoP: Personal Roving Presence", ACM:CHI Proceedings of CHI '98, 1998, 8 pages.
Paulos et al., "Social Tele-Embodiment Understanding Presence", Autonomous Robots, vol. 11, Issue 1, Kluwei Academic Publishers, Jul. 2001, pp. 87-95.
Paulos et al., "Ubiquitous Tele-Embodiment Applications and Implications", International Journal of Human Computer Studies, vol. 46, No. 6, Jun. 1997, pp. 861-877.
Paulos, Eric John Canny, "Video of PRoP 2 at Richmond Field Station", www.prop.org Printout of Home Page of Website and two-page Transcript of the audio portion of said PRoP Video, May 2001, 2 pages.
Picturetel Corporation, "PictureTel Live200 for Windows NT Product Guide", 1997, 63 pages.
Pin et al., "A New Family of Omnidirectional and Holonomic Wheeled Platforms for Mobile Robots", IEEE Transactions an Robotics and Automation, vol. 10, No. 4, Aug. 1994, pp. 480-489.
Piquepaille, Roland, "This Blog and its RSS Feed Are Moving", Roland Piquepaille's Technology Trends, How new technologies are modifying our way of life, Oct. 31, 2004, 2 pages.
West et al., "Design of Ball Wheel Mechanisms for Omnidirectional Vehicles with Full Mobility and Invariant Kinematics", Journal of Mechanical Design, vol. 119, Jun. 1997, pp. 153-161.
Yamasaki et al., "Applying Personal Robots and Active Interface to Video Conference Systems", 6th International Conference on Human Computer Interaction, vol. B, 1995, pp. 243-248.
Yamauchi, Brian, "PackBot: A Versatile Platform for Military Robotics", Proceedings of SPIE for Military Robotics, 2004, pp. 228-237.
Yong et al., "Robot Task Execution with Telepresence Using Virtual Reality Technology", 1998 International Conference on Mechatronic Technology, Nov. 30-Dec. 2, 1998, pp. 1-8.
Zambroski, James, "CMU, Pitt Developing 'Nursebot'", available online at <http://www.cs.cmu.edu/~nursebot/web/press/tribunereview.html>, Oct. 27, 2000, 3 pages.
Radvision, "Making Sense of Bandwidth the Netsense Way", Network Congestion in Unmanaged Networks Bandwidth Estimation and Adaptation Techniques, White Paper, Radvision's Netsense Technology, 2010, 7 pages.
Reynolds et al., "Review of Robotic Telemedicine Utilization in Intensive Care Units (ICUs)", 11th Annual ATA Symposium, Tampa, Florida, 2011, 1 page.
Roach, Adam, "Automatic Call Back Service in SIP", Internet Engineering Task Force, Internet Draft, Category: Informational, Mar. 2000, 8 pages.
Rovetta et al., "A New Telerobotic Application: Remote Laparoscopic Surgery Using Satellites and optical fiber Networks for Data Exchange", International Journal of Robotics Research, vol. 15, No. 3, Jun. 1, 1996, pp. 267-279.
Roy et al., "Towards Personal Service Robots for the Elderly", Workshop on Interactive Robots and Entertainment (WIRE 2000), available online at <http://www.ri.cmu.edu/pb_files/pub2/roy_nicholas_2000_1/roy_nicholas_2000_1.pdf>, vol. 25, 30 Apr.-May 1, 2000, 7 pages.
Sachs et al., "Virtual Visit: Improving Communication for Those Who Need it Most", Studies in Health Technology and Informatics, vol. 94, Medicine Meets Virtual Reality 11, 2003, pp. 302-308.
Salemi et al., "MILO: Personal Robot Platform", IEEE/RSJ International Conference on Intelligent Robots and Systems, Aug. 2005, pp. 4089-4094.
Sandt et al., "Perceptions for a Transport Robot in Public Environments", Proceedings of the 1997 IEEE/RSJ International Conference on Intelligent Robots and Systems, vol. 1, Sep. 7-11, 1997, pp. 360-365.
Sawyer, Robert J., "Inventing the Future: 2000 Years of Discovery", available online at <http://www.sfwriter.com/pritf.htm>, Jan. 2, 2000, 2 pages.
Schaeffer et al., "Care-O-BotTM: The Concept of a System for Assisting Elderly or Disabled Persons in Home Environments", Proceedings of the 24th Annual Conference of the IEEE Industrial Electronics Society, vol. 4, 1998, pp. 2476-2481.
Schraft et al., "Care-O-bot™: The Concept of a System for Assisting Elderly or Disabled Persons in Home Environments", IEEE Proceedings of the 24th Annual Conference of the Industrial Electronics Society, IECON '98, Aug. 31-Sep. 4, 1998, pp. 2476-2481.
Schultz et al., "Web Interfaces for Mobile Robots in Public Places", IEEE Robotics & Automation Magazine, vol. 7, No. 1, Mar. 2000, pp. 48-56.
Shimoga et al., "Touch and Force Reflection for Telepresence Surgery", Proceedings of the 16th Annual International Conference of the IEEE Engineering in Medicine and Biology Society, Nov. 1994, pp. 1049-1050.
Siegwart et al., "Interacting Mobile Robots on the Web", Proceedings of the 1999 IEEE International Conference on Robotics and Automation, May 1999, pp. 1-7.
Simmons et al., "Xavier: An Autonomous Mobile Robot on the Web", IEEE Robotics and Automation Magazine, 1999, pp. 43-48.
Stephenson, Gary, "Dr. Robot Tested at Hopkins", available online at <http://www.hopkinsmedicine.org/press/2003/august/030805.htm>, Aug. 5, 2003, 2 pages.
Stoianovici et al., "Robotic Tools for Minimally Invasive Urologic Surgery", Complications of Urologic Laparoscopic Surgery: Recognition, Management and Prevention, Dec. 2002, 17 pages.
Suplee, Curt, "Mastering the Robot", The Washington Post, Washington Post Staff Writer, Sep. 17, 2000, 5 pages.
Tahboub et al., "Dynamics Analysis and Control of a Holonomic Vehicle With Continuously Variable Transmission", Transactions of the ASME, Journal of Dynamic Systems, Measurement and Control, vol. 124, Mar. 2002, pp. 118-126.
Telepresence Research, Inc., "The Telepresence Mobile Robot System", available online at <http://www.telepresence.com/telepresence-research/TELEROBOT/>, Feb. 20, 1995, 3 pages.
Tendick et al., "Human-Machine Interfaces for Minimally Invasive Surgery", Proceedings of the 19th Annual International Conference of the IEEE Engineering in Medicine and Biology Society, vol. 6, Oct. 30-Nov. 2, 1997, pp. 2771-2776.
Theodosiou et al., "MuLVAT: A Video Annotation Tool Based on XML-Dictionaries and Shot Clustering", 19th International Conference, Artificial Neural Networks—ICANN 2009, Part II, Sep. 14-17, 2009, pp. 913-922.
Thrun et al., "Probabilistic Algorithms and the Interactive Museum Tour-Guide Robot Minerva", International Journal of Robotics Research, vol. 19, 2000, pp. 1-35.
Time, Lists, "Office Coworker Robot", Best Inventions of 2001, available online at <http://content.time.com/time/specials/packages/article/0,28804,1936165_1936255_1936640,00.html>, Nov. 19, 2001, 2 pages.
Tipsuwan et al., "Gain Adaptation of Networked Mobile Robot to Compensate QoS Deterioration", 28th Annual Conference of the Industrial Electronics Society, vol. 4, Nov. 5-8, 2002, pp. 3146-3151.
Tsui et al., "Exploring Use Cases for Telepresence Robots", 6th ACM/IEEE International Conference on Human-Robot Interaction (HRI), Mar. 2011, pp. 11-18.
Tyrrell et al., "Teleconsultation in Psychology: The Use of Videolinks for Interviewing and Assessing Elderly Patients", Age and Ageing, vol. 30, No. 3, May 2001, pp. 191-195.

(56) References Cited

OTHER PUBLICATIONS

Tzafestas et al., "VR-Based Teleoperation of a Mobile Robotic Assistant: Progress Report", Technical Report DEMO 2000/13, Institute of Informatics and Telecommunications, National Center for Scientific Research "Demokritos", Nov. 2000, pp. 1-23.
UMASS Lowell Robotics Lab, "Robotics Lab @ UMASS Lowell", Brochure, 2011, 2 pages.
Urquhart, Kim, "InTouch's Robotic Companion 'Beams Up' Healthcare Experts", Medical Device Daily, vol. 7, No. 39, Feb. 27, 2003, pp. 1, 4.
Video Middleware Cookbook, "H.350 Directory Services for Multimedia", 2 pages.
Weaver et al., "Monitoring and Controlling Using the Internet and Java", Proceedings of the 25th Annual Conference of the IEEE Industrial Electronics Society, vol. 3, 1999, pp. 1152-1158.
Weiss et al., "PEBBLES: A Personal Technology for Meeting Education, Social and Emotional Needs of Hospitalised Children", Personal and Ubiquitous Computing, vol. 5, No. 3, Aug. 2001, pp. 157-168.
Jouppi et al., "BiReality: Mutually-Immersive Telepresence", Proceedings of the 12th Annual ACM International Conference on Multimedia, Oct. 10-16, 2004, pp. 860-867.
Jouppi et al., "First Steps Towards Mutually-Immersive Mobile Telepresence", Proceedings of the 2002 ACM Conference on Computer Supported Cooperative Work, Nov. 16-20, 2002, pp. 354-363.
Kanehiro et al., "Virtual Humanoid Robot Platform to Develop Controllers of Real Humanoid Robots without Porting", IEEE/RSJ International Conference on Intelligent Robots and Systems, vol. 2, 2001, pp. 1093-1099.
Kaplan et al., "An Internet Accessible Telepresence", Multimedia Systems Journal, vol. 5, 1996, 7 pages.
Keller et al., "Raven Interface Project", The National Aviary's Teleconferencing Carnegie Mellon University Robot, Interaction and Visual Interface Design, School of Design, Carnegie Mellon University, 2001, 8 pages.
Khatib et al., "Robots in Human Environments", Proceedings International Conference on Control, Automation, Robotics, and Vision ICRACV2000, 1999, 15 pages.
Knight et al., "Active Visual Alignment of a Mobile Stereo Camera Platform", IEEE International Conference on Robotics and Automation, vol. 4, Apr. 24-28, 2000, pp. 3203-3208.
Koenen, Rob, "MPEG-4: a Powerful Standard for Use in Web and Television Environments", (KPN Research), available online at <http://www.w3.org/Architecture/1998/06/Workshop/paper26>, Jul. 1, 1998, 4 pages.
Kurlowicz et al., "The Mini Mental State Examination (MMSE)", Try This: Best Practices in Nursing Care to Older Adults, A series from the Hartford Institute of Geriatric Nursing, Issue No. 3, Jan. 1999, 2 pages.
Kuzuoka et al., "Can The GestureCam Be a Surrogate?", Proceedings of the Fourth European Conference on Computer-Supported Cooperative Work, 1995, pp. 181-196.
Lane, Earl, "Automated Aides", Available online at <http://www.cs.cum.edu/nursebot/web/press/nd4380.htm>, Oct. 17, 2000, 4 pages.
Lee et al., "A Novel Method of Surgical Instruction: International Telementoring", World Journal of Urology, vol. 16, No. 6, Dec. 1998, pp. 367-370.
Leifer et al., "VIPRR: A Virtually In Person Rehabilitation Robot", Proceedings of 1997 International Conference on Rehabilitation Robotics, Apr. 14-15, 1997, 4 pages.
Lemaire, Edward, "Using Communication Technology to Enhance Rehabilitation Services: A Solution Oriented User Manual", Institute for Rehabilitation Research and Development, Terry Fox Mobile Clinic, The Rehabilitation Centre, Ottawa, Ontario, Canada, Version 2.0, available online at <http://www.irrd.ca/telehealth/distfile/distman_v2_1.pdf>, 1998-2001, 104 pages.
Library of Congress, "008—Fixed-Length Data Elements (NR)", MARC 21 Format for Classification Data, available online at <http://www.loc.gov/marc/classification/cd008.html>, Jan. 2000, pp. 1-14.

Lim et al., "Control to Realize Human-Like Walking of a Biped Humanoid Robot", IEEE International Conference on Systems, Man, and Cybernetics, 2000, vol. 5, 2000, pp. 3271-3276.
Linebarger et al., "Concurrency Control Mechanisms for Closely Coupled Collaboration in Multithreaded Virtual Environments", Department of Computer Science and Engineering, Lehigh University, vol. 13, 2004, 40 pages.
Long, William F., "Robot Navigation Technology", available online at <http://www.atp.nist.gov/eao/sp950-1/helpmate.htm>, Mar. 1999, 3 pages.
Luna, Nancy, "Robot a New Face on Geriatric Care", ocregister.com, Aug. 6, 2003, 3 pages.
Mack, Michael J., "Minimally Invasive and Robotic Surgery", The Journal of the American Medical Association, vol. 285, No. 5, 2001, pp. 568-572.
Mair, G. M., "Telepresence—The Technology and its Economic and Social Implications", Technology and Society, 1997. 'Technology and Society at a Time of Sweeping Change'. Proceedings, 1997 International Symposium, Jun. 20-21, 1997, pp. 118-124.
Martin, Anya, "Brighter Days Ahead", Assisted Living Today, vol. 9, Nov./Dec. 2002, pp. 19-22.
McCardle et al., "The Challenge of Utilizing New Technology in Design Education", Loughborough University, IDATER 2000, 2000, pp. 122-127.
Meng et al., "E-Service Robot in Home Healthcare", Proceedings of the 2000 IEEE/RSJ, International Conference on Intelligent Robots and Systems, 2000, pp. 832-837.
Meiz, Cade, "HP Labs", available online at <http://www.pcmag.com/article2/0,2817,1130820,00.asp>, Jul. 4, 2003, 4 pages.
Michaud, Anne, "Introducing "Nursebot"", available online at <http://www.cs.cmu.edu/nursebot/web/press/globe 301/index.html>, 2001, 4 pages.
Microsoft Corporation, Inc., "Microsoft NetMeeting 3 Features excerpt from Official Microsoft NetMeeting 3.0 Book", available online at <http://technet.microsoft.com/en-us/library/cc723477.aspx>, 2012, 6 pages.
Minsky, Marvin, "Telepresence", OMNI Magazine, Jun. 1980, 6 pages.
Montemerlo, Reddy Whittaker, "Telepresence: Experiments in Next Generation Internet", available online at <http://www.ri.cmu.edu/creative/archives.htm>, Oct. 20, 1998, 3 pages.
Murphy, Robin R., "Introduction to AI Robotics", A Bradford Book, The MIT Press, Cambridge, Massachusetts, London, England, 2000, 487 pages.
Nakajima et al., "A Multimedia Teleteaching System using an Electronic Whiteboard for Two Way Communication of Motion Videos and Chalkboards", 2nd IEEE International Workshop on Robot and Human Communication, 1993, pp. 436-441.
Nakazato et al., "Group-Based Interface for Content-Based Image Retrieval", Proceedings of the Working Conference on Advanced Visual Interfaces, 2002, pp. 187-194.
Nakazato et al., "ImageGrouper: A Group-Oriented User Interface for Content-Based Image Retrieval and Digital Image Arrangement", Journal of Visual Languages & Computing, vol. 14, No. 4, Aug. 2003, pp. 45-46.
Nersc, "Berkeley Lab's RAGE Telepresence Robot Captures R&D100 Award", Available online at <https://www.nersc.gov/news-publications/news/nersc-center-news/2002/berkeley-lab-s-rage-telepresence-robot-captures-r-and-d100-award/>, Jul. 2, 2002, 2 pages.
Nomadic Technologies Inc., "Nomad XR4000 Hardware Manual", Release 1.0, Mar. 1999, 34 pages.
Noritsugu et al., "Application of Rubber Artificial Muscle Manipulator as a Rehabilitation Robot", Mechatronics, IEEE/ASME Transactions, vol. 2, No. 4, Dec. 1997, pp. 259-267.
North, Michael, "Telemedicine: Sample Script and Specifications for a Demonstration of Simple Medical Diagnosis and Treatment Using Live Two-Way Video on a Computer Network", Greenstar Corporation, 1998, 5 pages.
Ogata et al., "Development of Emotional Communication Robot: WAMOEBA-2R—Experimental Evaluation", Proceedings of the 2000 IEEE/RSJ International Conference on Intelligent Robots and Systems, vol. 1, 2000, pp. 175-180.

(56) References Cited

OTHER PUBLICATIONS

Ogata et al., "Emotional Communication Robot: WAMOEBA-2R—Emotion Model and Evaluation Experiments", Proceedings of the International Conference on Humanoid Robots, 2000, pp. 1-16.

Oh et al., "Autonomous Battery Recharging for Indoor Mobile Robots", Proceedings of Australian Conference on Robotics and Automation, 2000, pp. 1-6.

Ojha, Anand K., "An application of Virtual Reality in Rehabilitation", Proceedings of the 1994 IEEE Southeastcon 94 Creative Technology Transfer—A Global Affair, Apr. 1994, pp. 4-6.

Osborn, Jim, "Quality of Life Technology Center", QoLT Research Overview: A National Science Foundation Engineering Research Center, Carnegie Mellon University of Pittsburgh, 2 pages.

Panusopone et al., "Performance comparison of MPEG-4 and H.263+ for streaming video applications", Circuits Systems Signal Processing, vol. 20, No. 3, 2001, pp. 293-309.

Paulos et al., "A World Wide Web Telerobotic Remote Environment Browser", Available online at <http://www.w3.org/Conferences/WWW4/Papers/326/>, 1995, 15 pages.

Paulos et al., "Designing Personal Tele-Embodiment", Proceedings of IEEE International Conference on Robotics and Automation, vol. 4, May 16-20, 1998, pp. 3173-3178.

Paulos, Eric J., "Personal Tele-Embodiment", Dissertation, Doctor of Philosophy in Computer Science in the Graduate Division of the University of California at Berkeley, 2001, 282 pages.

Weiss et al., "Telework and Video-Mediated Communication: Importance of Real-Time, Interactive Communication for Workers with Disabilities", available online at <http://www.telbotics.com/research_3.htm>, retrieved on Nov. 23, 2010, 3 pages.

Zamrazil, Kristie, "Telemedicine in Texas: Public Policy Concerns", Focus Report, House Research Organization, Texas House of Representatives, No. 76-22, May 5, 2000, pp. 1-16.

Zipperer, Lorri, "Robotic Dispensing System", ISMP Medication Safety Alert!, vol. 4, No. 17, Aug. 25, 1999, 2 pages.

Zorn, Benjamin G., "Ubiquitous Telepresence", Depailment of Computer Science, University of Colorado, 1996, 13 pages.

\* cited by examiner

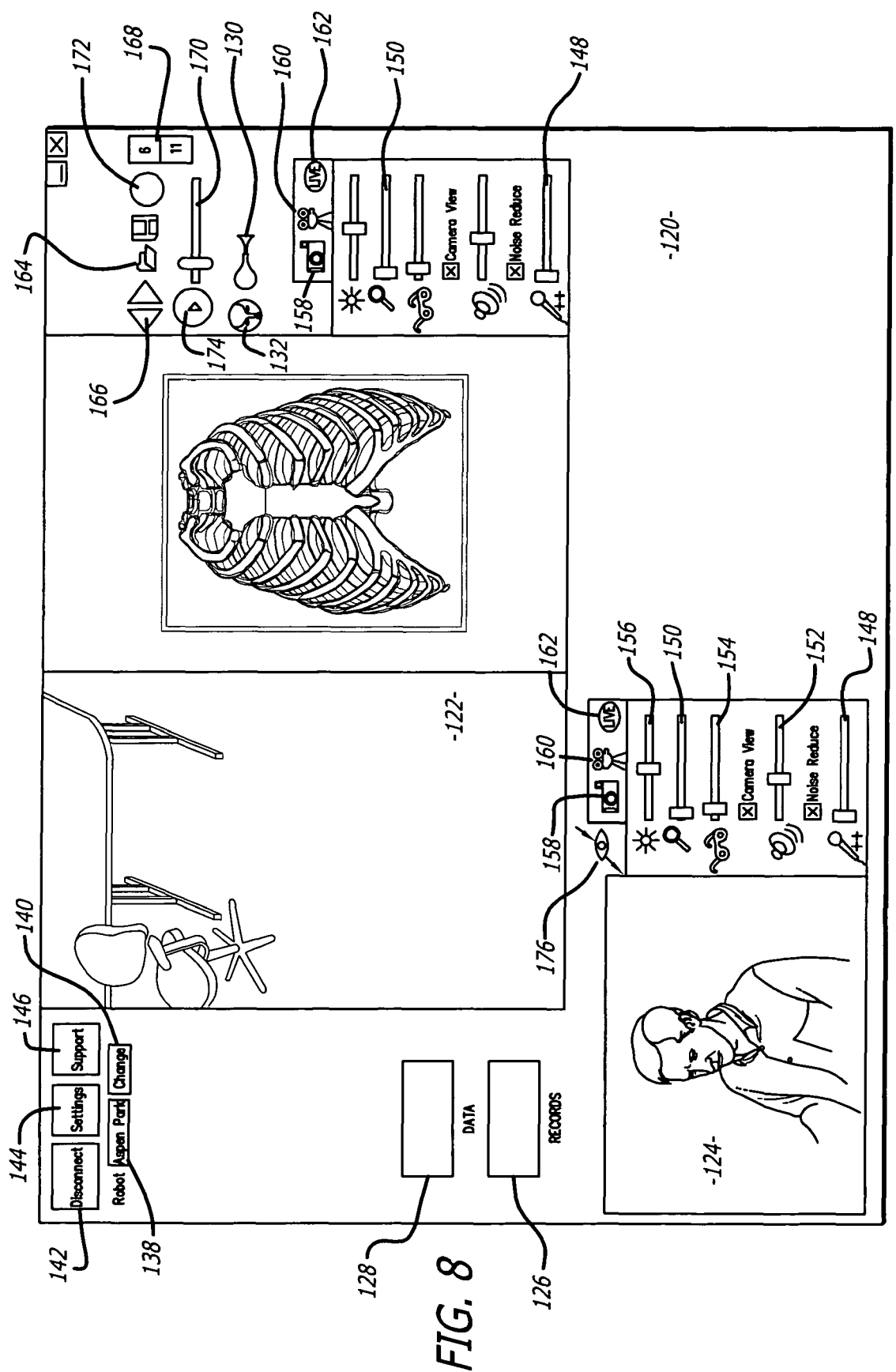

REMOTE PRESENCE SYSTEM MOUNTED TO OPERATING ROOM HARDWARE

BACKGROUND OF THE INVENTION

1. Field of the Invention

The subject matter disclosed generally relates to the field of robotic tele-presence systems.

2. Background Information

When performing a surgical procedure it is sometimes desirable to have a mentor assist in the procedure. Unfortunately, this typically requires that the mentor be at the surgical site which is not always practical. There has been developed a robotic system sold by Intuitive Surgical, Inc. under the trademark Da Vinci which allows a surgeon to remotely perform a surgical procedure through use of robot arms located at the surgical site. This allows a specialist to actually perform a procedure from a remote location. The Da Vinci system is both large and expensive and thus not available for every medical facility. It would be desirable to allow remote medical consultation with a system that was relatively inexpensive and easy to install into existing operating rooms.

BRIEF SUMMARY OF THE INVENTION

A robot system that includes a remote station and a robot face. The robot face includes a camera that is coupled to a monitor of the remote station and a monitor that is coupled to a camera of the remote station. The robot face and remote station also have speakers and microphones that are coupled together. The robot face may be coupled to a boom. Alternatively, the robot face may be attached to a medical table with an attachment mechanism.

BRIEF DESCRIPTION OF THE DRAWINGS

FIG. 8 is a display user interface showing an image and an electronic medical record being simultaneously displayed.

DETAILED DESCRIPTION

Disclosed is a robot system that includes a remote station and a robot face. The robot face includes a camera that is coupled to a monitor of the remote station and a monitor that is coupled to a camera of the remote station. The robot face and remote station also have speakers and microphones that are coupled together. The robot face may be coupled to a boom. The boom can extend from the ceiling of a medical facility. Alternatively, the robot face may be attached to a medical table with an attachment mechanism. The robot face and remote station allow a medical personnel to provide remote medical consultation through the system.

Figure 1:
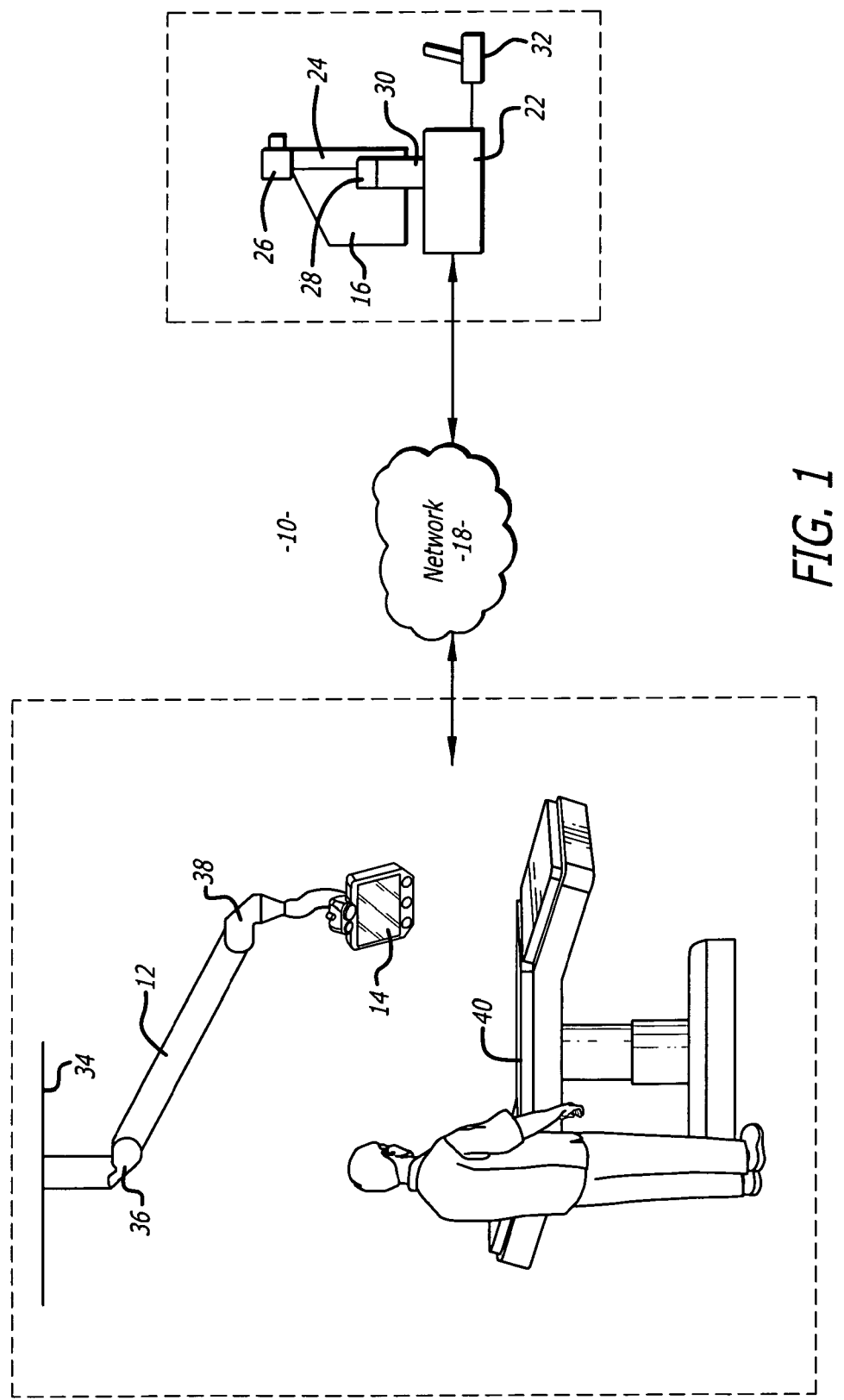
FIG. 1 is an illustration of a tele-presence system.
Figure 2:
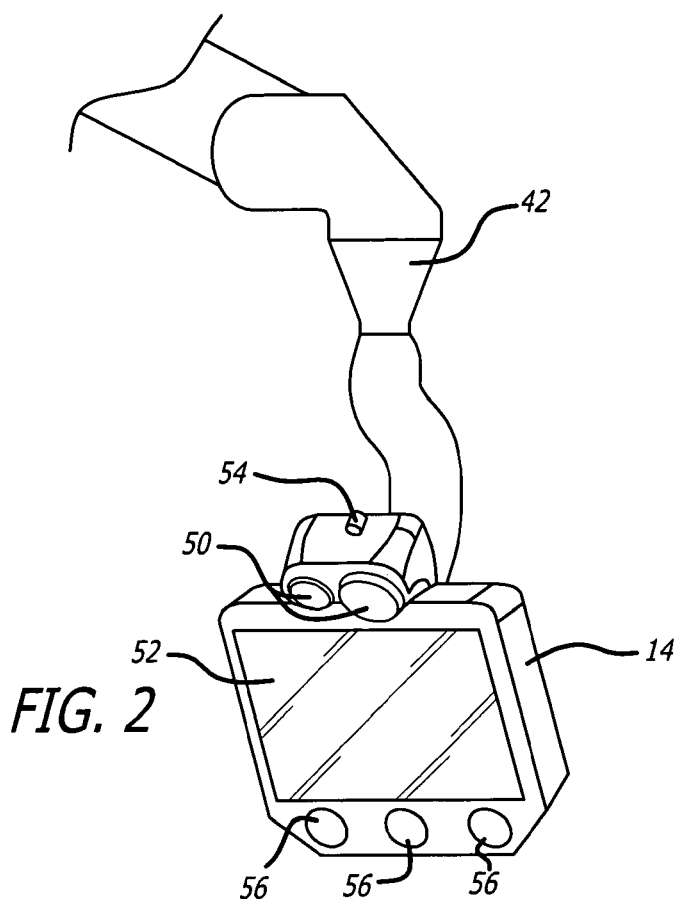
FIG. 2 is an enlarged view of a robot face of the system.
Figure 3:
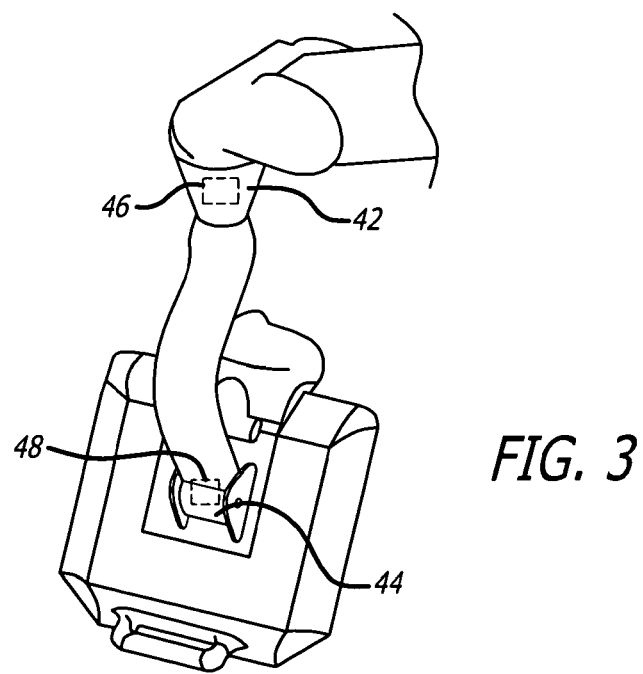
FIG. 3 is a rear view of the robot face.

Referring to the drawings more particularly by reference numbers, FIGS. 1, 2 and 3 show a tele-presence system 10. The system 10 includes a boom 12, a robot face 14 and a remote control station 16. The remote control station 16 may be coupled to the robot face 14 through a network 18. By way of example, the network 18 may be either a packet switched network such as the Internet, or a circuit switched network such as a Public Switched Telephone Network (PSTN) or other broadband system. Alternatively, the robot face 14 may be coupled to the remote station 16 network thru a satellite.

The remote control station 16 may include a computer 22 that has a monitor 24, a camera 26, a microphone 28 and a speaker 30. The computer 22 may also contain an input device 32 such as a joystick or a mouse. The control station 16 is typically located in a place that is remote from the robot face 14. Although only one remote control station 16 is shown, the system 10 may include a plurality of remote stations 16. In general any number of robot faces 14 may be coupled to any number of remote stations 16 or other robot faces 14. For example, one remote station 16 may be coupled to a plurality of robot faces 14, or one robot face 14 may be coupled to a plurality of remote stations 16, or a plurality of robot faces 14. The system may include an arbitrator (not shown) that control access between the robot face(s) 14 and the remote stations 16.

The boom 12 may extend from the ceiling 34 of a medical facility. The boom 12 may include articulate joints 36 and 38 that provide at least two degrees of freedom and allow a user to move the robot face 14 relative to an medical table 40 such as an operating room ("OR") table.

The boom 12 may have additional joints 42 and 44 that allow the robot face 14 to be panned and tilted, respectively. The joints 42 and 44 may contain actuators 46 and 48, respectively, that can be remotely actuated through manipulation of the input device 32 at the remote station 16.

Each robot face 14 includes a camera(s) 50, a monitor 52, a microphone(s) 54 and a speaker(s) 56. The robot camera 50 is coupled to the remote monitor 24 so that a user at the remote station 16 can view a patient on the table 40. Likewise, the robot monitor 52 is coupled to the remote camera 26 so personnel at the surgical site may view the user of the remote station 16. The microphones 28 and 54, and speakers 30 and 56, allow for audible communication between the system operator and the personnel at the surgical site.

The system 10 allows a system user such as a surgical specialist to view a patient on the table 40 and provide remote medical consultation through the remote station 16 and the robot face 14. Personnel at the surgical site can transmit questions and responses through the system back to the system operator. The robot camera 50 allows the specialist to view the patient and enhance the medical consultation. The robot monitor 52 can display the specialist to provide a feeling of presence at the surgical site. The boom 12 allows the personnel to move the robot face 14 into and out of the surgical area.

The robot face 14 can be retrofitted onto booms that presently exist in medical facilities. For example, some present medical facilities include a monitor attached to a boom. The existing monitor can be replaced with the robot face 14 that is then coupled to the remote station 16.

Figure 4:
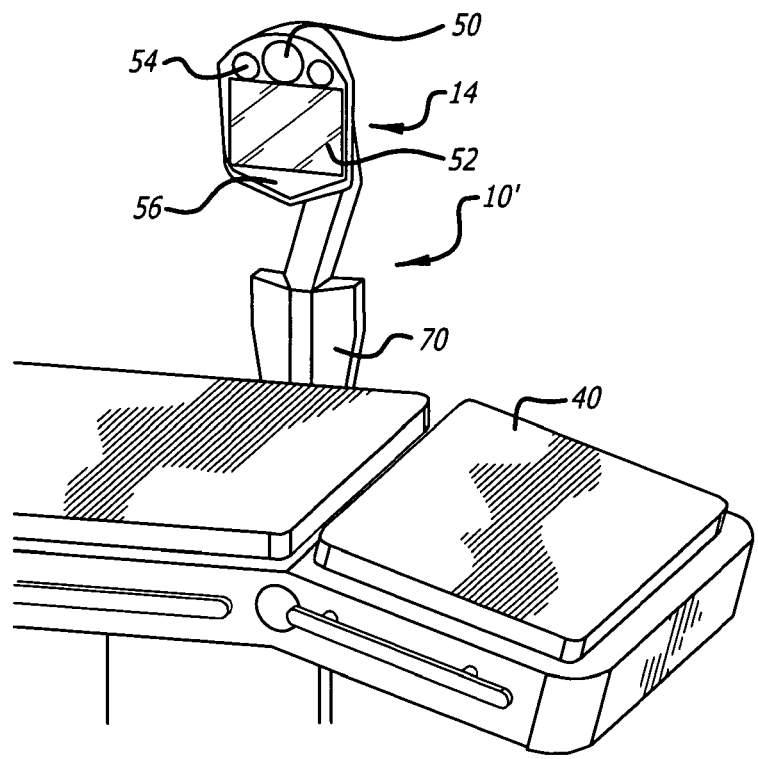
FIG. 4 is an illustration of an alternate embodiment of the tele-presence system.
Figure 5:
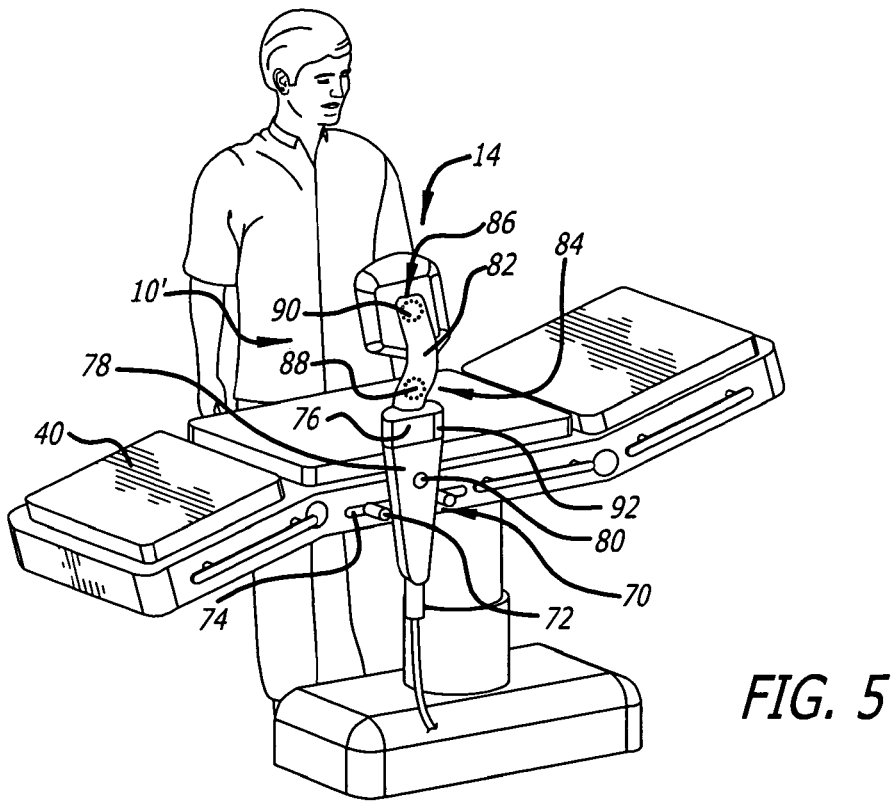
FIG. 5 is a rear view of a robot face of the embodiment shown in FIG. 4.

FIGS. 4 and 5 shows an alternate embodiment of a system 10' where the robot face 14 is attached to the table 40 with an attachment mechanism 70. The attachment mechanism 70 may include a pair of clamps 72 that are pressed into a rail 74 of the table 40. The attachment mechanism 70 may have a sleeve 76 that slides relative to a housing 78 so that a user can adjust the height of the robot face 14. The face position may be locked in place by rotation of knob 80.

The attachment mechanism 70 may include a neck portion 82 with joints 84 and 86 that allow for pan and tilt of the robot face 14, respectively. The joints 84 and 86 may be manually actuated or contain actuators 88 and 90, respectively, that can be actuated through the input device 32 at the remote station 16.

The attachment mechanism 70 may include handles 92 that allow a user to carry the robot face 14 to and from the table 40. The attachment mechanism 70 allows the robot face 14 to be readily utilized at a surgical site, particularly when the operating room does not have a boom.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

The systems 10 and 10' may have certain components and software that are the same or similar to a robotic system provided by the assignee InTouch-Health, Inc. of Santa Barbara, Calif. under the name RP-7 and embodies a system described in U.S. Pat. No. 6,925,357, which is hereby incorporated by reference.

Figure 6:
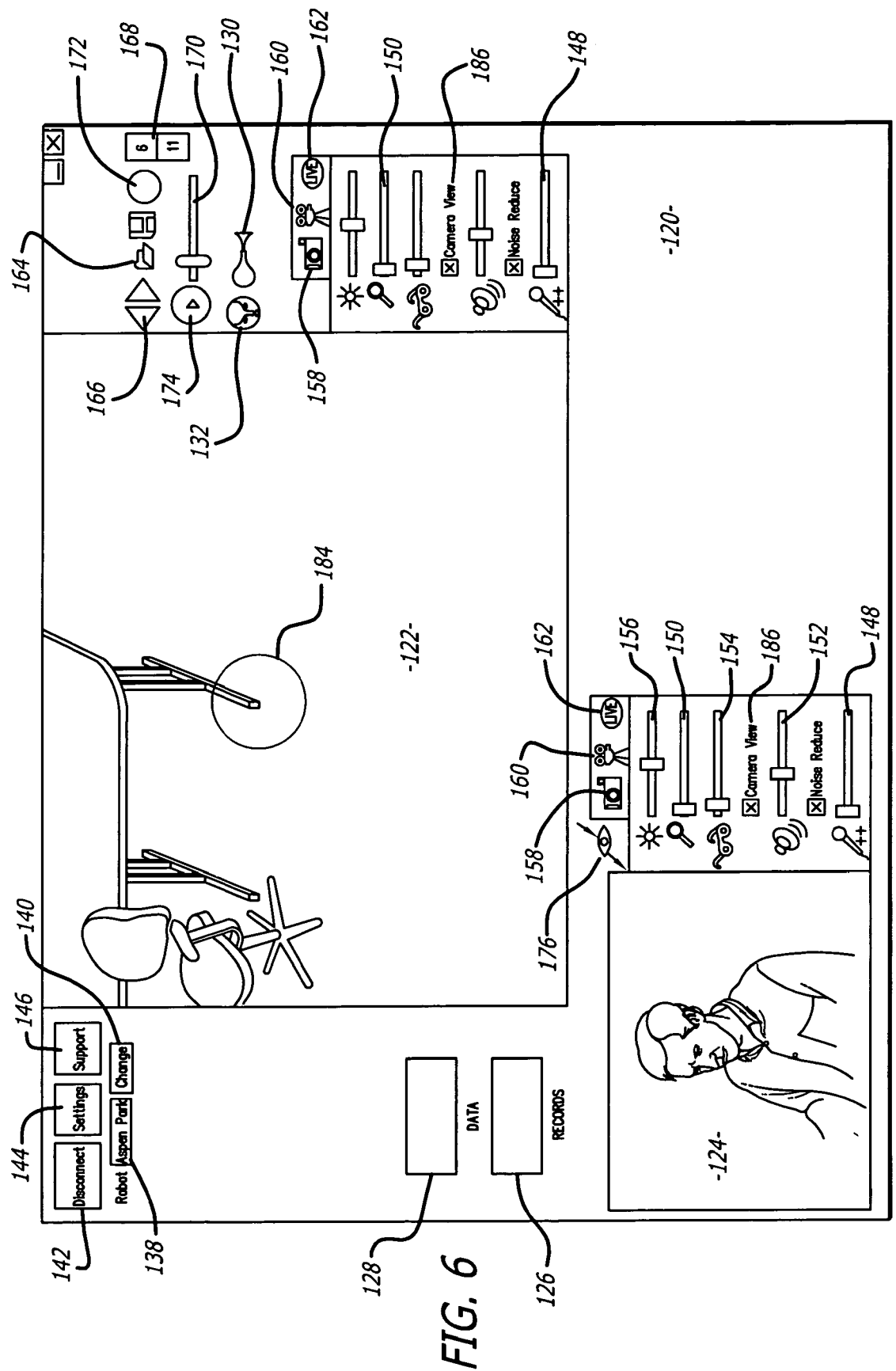
FIG. 6 is an illustration of a display user interface of a remote station.

FIG. 6 shows a display user interface ("DUI") 120 that can be displayed at the remote station 16. The DUI 120 may include a robot view field 122 that displays a video image captured by the camera of the robot face 14. The DUI 120 may also include a station view field 124 that displays a video image provided by the camera of the remote station 16. The DUI 120 may be part of an application program stored and operated by the computer 22 of the remote station 16.

Figure 7:
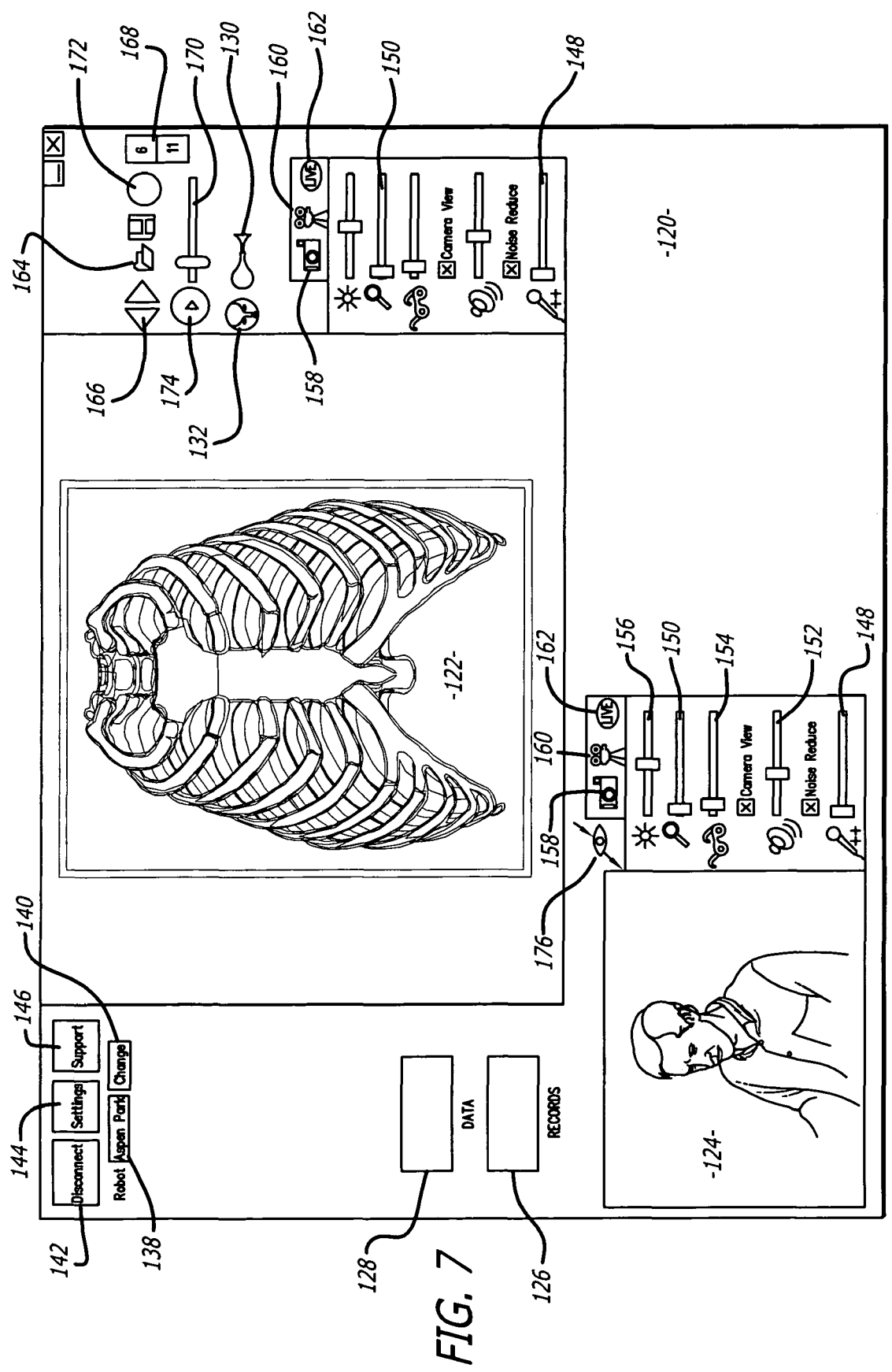
FIG. 7 is a display user interface showing an electronic medical record.

The DUI 120 may include a graphic button 126 that can be selected to display an electronic medical record as shown in FIG. 7. The button 126 can be toggled to sequentially view the video image and the electronic medical record. Alternatively, the view field 122 may be split to simultaneously display both the video image and the electronic medical record as shown in FIG. 8. The viewing field may allow the physician to modify the medical record by adding, changing or deleting all or part of the record. The remote clinician can also add to the medical record still images or video captured by the camera of the robot.

The DUI 120 may have a monitor data field 128 that can display the data generated by a medical monitoring device(s) (not shown) and transmitted to the remote station. The data can be added to the electronic medical record, either automatically or through user input. For example, the data can be added to a record by "dragging" a monitor data field 128 into the viewing field 122.

The DUI 120 may include alert input icons 130 and 132. Alert icon 130 can be selected by the user at the remote station to generate an alert indicator such as a sound from the speaker of the robot face 14. Selection of the icon generates an alert input to the robot face 14. The robot face 14 generates a sound through its speaker in response to the alert input. By way of example, the sound may simulate the noise of a horn. Consequently, the icon 130 may have the appearance of a horn.

Alert icon 132 can be selected to request access to the video images from the robot face. The default state of the robot may be to not send video information to the remote station. Selecting the alert icon 132 sends an alert input such as an access request to the robot face. The robot face then generates an alert indicator. The alert indicator can be a sound generated by the robot speaker, and/or a visual prompt on the robot monitor. By way of example, the visual prompt may be a "flashing" graphical icon. The sound may simulate the knocking of a door. Consequently, the alert icon 132 may have the appearance of a door knocker.

In response to the alert indicator the user may provide a user input such as the depression of a button on the robot face, or the selection of a graphical image on the robot monitor, to allow access to the robot camera. The robot face may also have a voice recognition system that allows the user to grant access with a voice command. The user input causes the robot face to begin transmitting video images from the robot camera to the remote station that requested access to the robot face. A voice communication may be established before the cycle of the alert input and response, to allow the user at the remote station to talk to the caller recipient at the robot face.

The DUI 120 may include a location display 138 that provides the location of the robot face. The CHANGE button 140 can be selected to change the default robot face in a new session. The CHANGE button 140 can be used to select and control a different robot face in a system that has multiple robot faces. The user can initiate and terminate a session by selecting box 142. The box 142 changes from CONNECT to DISCONNECT when the user selects the box to initiate a session. System settings and support can be selected through buttons 144 and 146.

Both the robot view field 122 and the station view field 124 may have associated graphics to vary the video and audio displays. Each field may have an associated graphical audio slide bar 148 to vary the audio level of the microphone and another slide bar 152 to vary the volume of the speakers.

The DUI 120 may have slide bars 150, 154 and 156 to vary the zoom, focus and brightness of the cameras, respectively. A still picture may be taken at either the robot face or remote station by selecting one of the graphical camera icons 158. The still picture may be the image presented at the corresponding field 122 or 124 at the time the camera icon 158 is selected. Capturing and playing back video can be taken through graphical icons 160. A return to real time video can be resumed, after the taking of a still picture, captured video, or reviewing a slide show, by selecting a graphical LIVE button 162.

A still picture can be loaded from disk for viewing through selection of icon 164. Stored still images can be reviewed by selecting buttons 166. The number of the image displayed relative to the total number of images is shown by graphical boxes 168. The user can rapidly move through the still images in a slide show fashion or move through a captured video clip by moving the slide bar 170. A captured video image can be paused through the selection of circle 174. Play can be resumed through the same button 174. Video or still images may be dismissed from the active list through button 172. Video or still images may be transferred to the robot by selecting icon 176. For example, a doctor at the remote station may transfer an x-ray to the screen of the robot.

The system may provide the ability to annotate 184 the image displayed in field 122 and/or 124. For example, a doctor at the remote station may annotate some portion of the image captured by the robot face camera. The annotated image may be stored by the system. The system may also allow for annotation of images sent to the robot face through icon 176. For example, a doctor may send an x-ray to the robot face which is displayed by the robot screen. The doctor can annotate the x-ray to point out a portion of the x-ray to personnel located at the robot site. This can assist in allowing the doctor to instruct personnel at the robot site.

The display user interface may include graphical inputs 186 that allow the operator to turn the views of the remote station and remote cameras on and off.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A tele-presence system, comprising:
   a boom attached to a fixed structure at a first location; and,
   a robot face coupled to said boom, said robot face including a robot monitor, a robot camera, a robot speaker, and a robot microphone, wherein the robot face is configured to:
      communicate with a remote control station at a second location via a network;
      display an image captured by a camera of the remote control station on the robot monitor;
      transmit an image captured by the robot camera to the remote control station for display on a monitor of the remote control station;
      reproduce, via the robot speaker, a sound captured by a microphone of the remote control station;
      transmit a sound captured by the robot microphone to the remote control station for reproduction by a speaker of the remote control station;
      pan relative to the boom in response to input from a user received via a user input device of the remote control station; and,
      tilt relative to the boom in response to input from a user received via a user input device of the remote control station.

2. The system of claim 1, wherein said boom has at least two degrees of freedom.

3. The system of claim 1, wherein said remote station monitor displays a display user interface.

4. The system of claim 1, wherein said boom includes actuators to provide at least two degrees of freedom for said robot face.

5. The system of claim 4, wherein said remote station transmits commands to actuate said actuators.

6. The system of claim 1, further comprising a broadband network coupled to said robot face and said remote station.

7. The system of claim 1, further comprising a medical facility that supports said boom and a medical table that is in physical proximity to said robot face.

8. A method for providing a remote medical consultation, comprising:
   panning and tilting a robot face that is attached to a boom that is attached to a fixed structure at a first location in response to commands received from a remote station at a second location;
   transmitting an image from a camera of the robot face to a monitor of the remote station;
   displaying a user image received from a camera of the remote station on a monitor of the robot face; and,
   reproducing, via a speaker of the robot face, an audio command captured by a microphone of the remote station.

9. The method of claim 8, further comprising transmitting an audio request from a robot microphone to a station speaker.

10. The method of claim 8, further comprising receiving an actuator command from the remote station to actuate an actuator of the boom.

11. A tele-presence system that can be implemented with a medical table, comprising:
    a robot face at a first location, the robot face includes a monitor, a robot camera, a robot speaker and a robot microphone; and
    an attachment mechanism that attaches said robot face to the medical table; wherein the robot face is configured to:
       communicate with a remote control station at a second location via a network;
       display an image captured by a camera of the remote control station on the robot monitor;
       transmit an image captured by the robot camera to the remote control station for display on a monitor of the remote control station;
       reproduce, via the robot speaker, a sound captured by a microphone of the remote control station;
       transmit a sound captured by the robot microphone to the remote control station for reproduction by a speaker of the remote control station;
       pan relative to the medical table in response to input from a user received via a user input device of the remote control station; and,
       tilt relative to the medical table in response to input from a user received via a user input device of the remote control station.

12. The system of claim 11, wherein said attachment mechanism has at least one degree of freedom.

13. The system of claim 11, wherein said station monitor displays a display user interface.

14. The system of claim 11, wherein said attachment mechanism includes actuators to provide at least two degrees of freedom for said robot face.

15. The system of claim 14, wherein said remote station transmits commands to actuate said actuators.

16. The system of claim 11, further comprising a broadband network coupled to said robot face and said remote station.

17. The system of claim 11, wherein said attachment mechanism includes at least one clamp.

18. A method for providing a remote medical consultation, comprising:
    attaching a robot face to a medical table at a first location;
    panning and tilting the robot face relative to the medical table in response to commands received from a remote station at a second location
    transmitting an image from a camera of the robot face to a monitor of the remote station;
    displaying a user image received from a camera of the remote station on a monitor of the robot face; and,
    reproducing, via a speaker of the robot face, an audio command captured by a microphone of the remote station.

19. The method of claim 18, further comprising transmitting an audio request from a robot microphone to a station speaker.

20. The method of claim 18, further comprising receiving an actuator command from the remote station to actuate an actuator of said attachment mechanism.

* * * * *